United States Patent
Larson et al.

(10) Patent No.: US 7,585,369 B2
(45) Date of Patent: Sep. 8, 2009

(54) APPARATUS FOR COATING MEDICAL DEVICES

(76) Inventors: Marian L. Larson, 1464 Chuckanut Dr., Bellingham, WA (US) 98229; Eugene A Larson, 2457 W. Shore Dr., Lummi Island, WA (US) 98262

( * ) Notice: Subject to any disclaimer, the term of this patent is extended or adjusted under 35 U.S.C. 154(b) by 0 days.

(21) Appl. No.: 11/021,656

(22) Filed: Dec. 23, 2004

(65) Prior Publication Data

US 2006/0029722 A1    Feb. 9, 2006

Related U.S. Application Data

(60) Provisional application No. 60/598,656, filed on Aug. 4, 2004.

(51) Int. Cl.
*B05C 3/08* (2006.01)

(52) U.S. Cl. .............. 118/416; 118/417; 118/418; 118/421; 118/429; 118/641; 118/696

(58) Field of Classification Search ............ 118/417, 118/418, 416, 421, 429, 641, 696; 427/2.24, 427/242; 366/139, 220, 225, 228; 623/920
See application file for complete search history.

(56) References Cited

U.S. PATENT DOCUMENTS

| | | | | |
|---|---|---|---|---|
| 4,478,172 | A | | 10/1984 | Hertzler |
| 4,536,092 | A | * | 8/1985 | Kedem ................ 366/265 |
| 4,581,242 | A | * | 4/1986 | Forster ................ 427/2.18 |
| 5,443,801 | A | * | 8/1995 | Langford ............. 422/294 |
| 5,662,516 | A | * | 9/1997 | You ..................... 451/113 |
| 5,884,999 | A | * | 3/1999 | Muzzio et al. ........ 366/219 |
| 6,605,260 | B1 | * | 8/2003 | Busted ................. 422/186.3 |
| 7,105,198 | B2 | * | 9/2006 | Sundar ................. 427/2.24 |
| 2004/0062592 | A1 | | 4/2004 | Shekalim et al. |
| 2004/0261698 | A1 | * | 12/2004 | Roorda et al. ......... 118/416 |
| 2005/0120951 | A1 | * | 6/2005 | Spencer et al. ........ 118/420 |

FOREIGN PATENT DOCUMENTS

| | | |
|---|---|---|
| WO | WO 2004/012784 | 2/2004 |
| WO | WO 2004/060428 | 7/2004 |

* cited by examiner

*Primary Examiner*—Laura Edwards
(74) *Attorney, Agent, or Firm*—Robert L. McDowell

(57) ABSTRACT

An apparatus for coating medical devices at the point of care with a polymer and/or therapeutic agent comprising an environmentally controlled device coating chamber in which the device may be delivered by the manufacturer as the device packaging, or the device may be placed into the chamber at the point of care. The environmentally controlled chamber can provide a sterile enclosure in which the polymer and/or a therapeutic agent can be applied to an uncoated or previously coated device and converted to another form (such as a liquid to a film or gel) if desired, under controlled and reproducible conditions. The environmentally controlled chamber can accommodate and provide for coating the device by immersion, spray and other methods of covering the device surface with a liquid or powder. The chamber can provide for energy sources, both internally, such as heat produced by film heaters, and externally, such as UV light or microwave passing through the enclosure. The chamber may allow for changes in atmosphere to affect the coating, such as the introduction of certain gases and introducing pressure or vacuum.

41 Claims, 19 Drawing Sheets

APPARATUS FOR COATING MEDICAL DEVICES

This application claims the benefit of U.S. Provisional Patent Application No. 60/598,656 filed Aug. 4, 2004.

FIELD OF THE INVENTION

The present invention relates to the delivery of therapeutic agents from a coating, placed onto an implantable medical device at the point of care. More specifically, the present invention is directed to an environmentally controlled device coating and preparation chamber that facilitates the coating of a medical device with a drug and/or polymer coating at the point of care, prior to implantation into the body of a human or animal.

BACKGROUND OF THE INVENTION

Coating the surface of implanted medical devices with polymers and/or therapeutic agents has become a common practice. In 2004, drug eluding coronary stents are expected to comprise more than half of the over four billion dollar worldwide stent market. Therapeutic agents can enhance the intended effect of the medical device, reduce or eliminate infection or inflammation related to the device, accelerate or improve acceptance of the device by the body, and/or treat specific diseases at the site of the device.

Medical devices which are implanted into the human body and whose function can be enhanced by therapeutic coatings include artificial joints, fixation devices such as bone implants, artificial heart valves, pacemaker leads, dental implants and stents including cardiovascular, esophageal, and biliary.

Polymers and coatings such as phosphorycholine, hydrogels and hydroxyapatite, with and without additional therapeutic agents, are commonly placed onto the surface of medical devices at the point of manufacture. While this practice delivers the device ready to use at the point of care, the coating and/or therapeutic agents are subjected to the device sterilization process and the rigors of handling, shipping and storage. Many therapeutic agents, such as proteins, cannot survive the device sterilization. Also, many therapeutic agents have relatively short shelf lives compared to the device itself, and when placed on the device at the point of manufacture, limit the shelf life and storage condition of the device.

Larson et al., in U.S. Pat. No. 6,309,380, address the device point of manufacture therapeutic coating limitation problem by providing for application of the therapeutic coating at the point of care where and when the device is placed into the patient's body. This is accomplished by coating the device at the point of care immediately prior to implantation with a polymer and/or therapeutic agent and converting the coating to a film by a chemical process or energy source such as heat or UV light. Larson et al. do not provide for applying a coating and/or drug to the device at the point of care in a manner that reproducibly controls the device sterility and factors affecting variability of the coating, and subsequently the drug delivery after implantation of the device.

SUMMARY OF THE INVENTION

The present invention is directed to an apparatus for coating medical devices at the point of care, such as in hospitals and medical clinics, for example, with a polymer and/or therapeutic agent. The invention provides for a point of care environmentally controlled device coating chamber (ECDCC) in which the device may be delivered by the manufacturer as the device packaging, or the device may be placed into the chamber at the point of care. The environmentally controlled chamber provides a sterile enclosure in which the solution containing polymer and/or a therapeutic agent can be applied to the device, and converted to a film if desired, under controlled and reproducible conditions. The environmentally controlled chamber of the invention can accommodate and provide for coating the device by immersion, spray and other methods of covering the device surface with a liquid or powder. The chamber of this invention can provide for energy sources, both internally, such as heat produced by film heaters, and externally, such as light (e.g. UV) or microwave passing through the enclosure. The chamber may allow for changes in atmosphere to affect the coating, such as the introduction of certain gases and introducing pressure or vacuum. In addition, the present invention provides for an electronically, and/or manually, controlled machine (hereafter called a "docking station") which can be used to electro-mechanically, and/or manually, hold, position, and/or manipulate an ECDCC for the purpose of mixing medical device coating materials, introducing one or more substances into an ECDCC, and/or otherwise controlling the environment for, and/or the process of, the application of therapeutic, and/or other substances to one or more medical devices within an ECDCC.

DETAILED DESCRIPTION OF THE PREFERRED EMBODIMENTS

Figure 1:
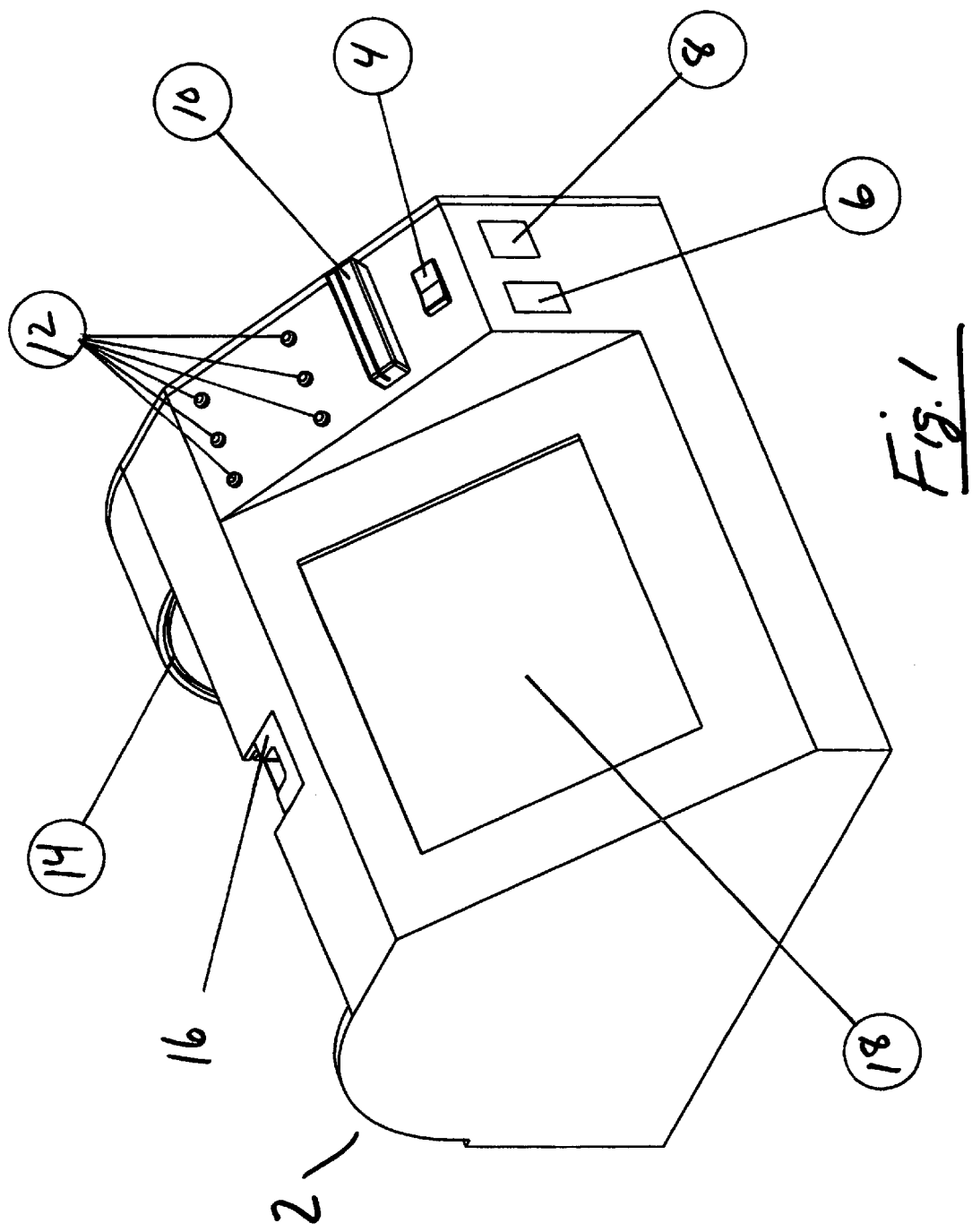
FIG. 1 illustrates the operator's panel and display of a docking station.

Coating a medical device with a therapeutic agent at the point of care requires a process and procedure which delivers a reproducibly and controlled dose of the therapeutic agent and a coating which has reproducible adhesion and mechanical properties. The coating process must be done in a manner which preserves the sterility of the device, coating polymer and/or therapeutic agent. The application of energy to facilitate the formation of coatings must be done in a manner that is uniform, reproducible and does not degrade the therapeutic agent. In addition, the placement of therapeutic agents onto the device at the point of care cannot be technique dependent nor require specialized skill or unusual attention by attending medical personnel. It is anticipated that many point of care device coatings, intended to provide a therapeutic effect and enhance the action of the device, will be applied to the device during or immediately prior to a surgery or other invasive procedures.

As stated above, the present invention is directed to an apparatus for coating medical devices, such as with a polymer and/or therapeutic agent, at the point of care. The invention provides for a coating chamber which is positionable in a docking station. The environmentally controlled device coating chamber may contain a port for adding the coating material (while maintaining sterility of the device, chamber and solution) and a heater to provide temperature controlled heat for the film formation process. It may also contain a stirring means (e.g. a magnetic field driven stirrer) for thoroughly mixing the polymer and the therapeutic agent prior to the coating process. A second heater may be contained in the base of the coating chamber for heating the coating solution to a specific temperature before the coating process begins. The coating chamber can incorporate a reservoir, with or without a one-way valve, to trap excess polymer and/or therapeutic liquid or powder during and after the coating process. The coating chamber can be fabricated from materials such as certain plastics, which provide for the passage of UV light and/or microwave energy to facilitate film formation.

The coating chamber can be received by a docking station that can provide timed and controlled energy (light, microwave, etc.) or electrical power to the device, and a timed rotating magnetic field to drive the magnetic stirrer incorporated in the coating chamber and timed and controlled rotation of the coating chamber to facilitate complete and uniform distribution of the solution or powder on the device.

FIGS. 1-4 illustrate one aspect of the present invention comprising a docking station 2 into which various coating chambers (described below) are positionable for coating of a medical device. The docking station 2 (FIG. 1) includes an operator's panel comprising an on-off switch 4, bar code reader 6, chip reader 8, swipe card reader 10 and indicator lights 12. A mechanism to read information stored on a computer disc may also be included. A groove 14 is provided in the docking station chassis 15 for a rollup door (shown with door "open") and an electronically controlled rollup door latch 16, 17 (FIG. 3) restricts and/or controls coating processes so that the door remains closed during processing. A touch screen interactive display 18 receives feedback, such as from an internal level detector, and provides for an interactive readout such as from an out-of-level system lock.

Figure 2:
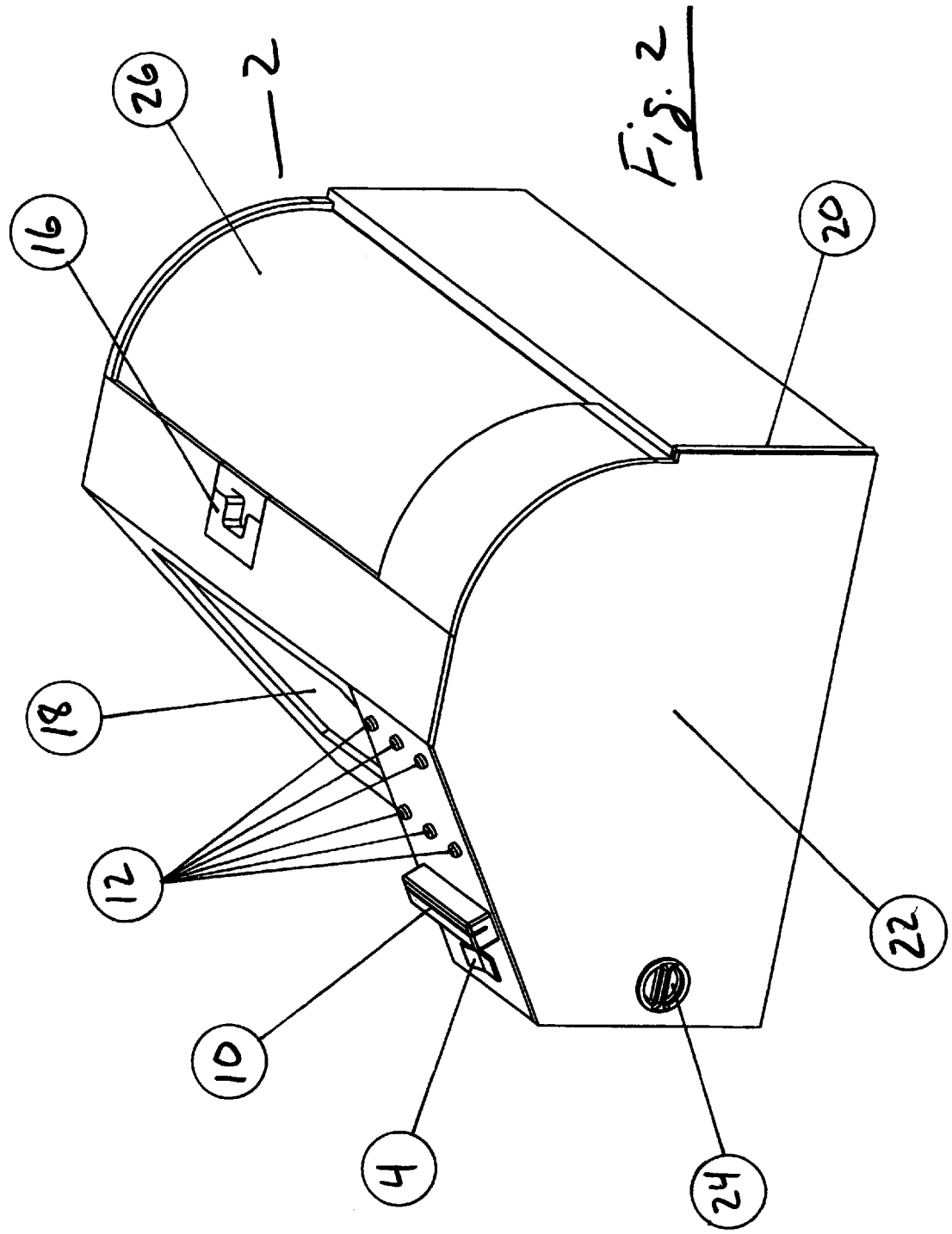
FIG. 2 shows the docking station side door and chamber process area with door in closed position.

As best seen in FIG. 2, the docking station 2 preferably includes a piano-style side door hinge 20, side door 22 and door latch 24, preferably electronically controlled. Further included is a rollup door 26 (closed position) enclosing a coating chamber process area 28 (FIGS. 3 and 4 with door 26 open) having one or more, preferably three, reflective interior surfaces 30 and one or more bulbs or other devices 32 for introducing light, heat and/or microwave radiation to the chamber 28.

Figure 3:
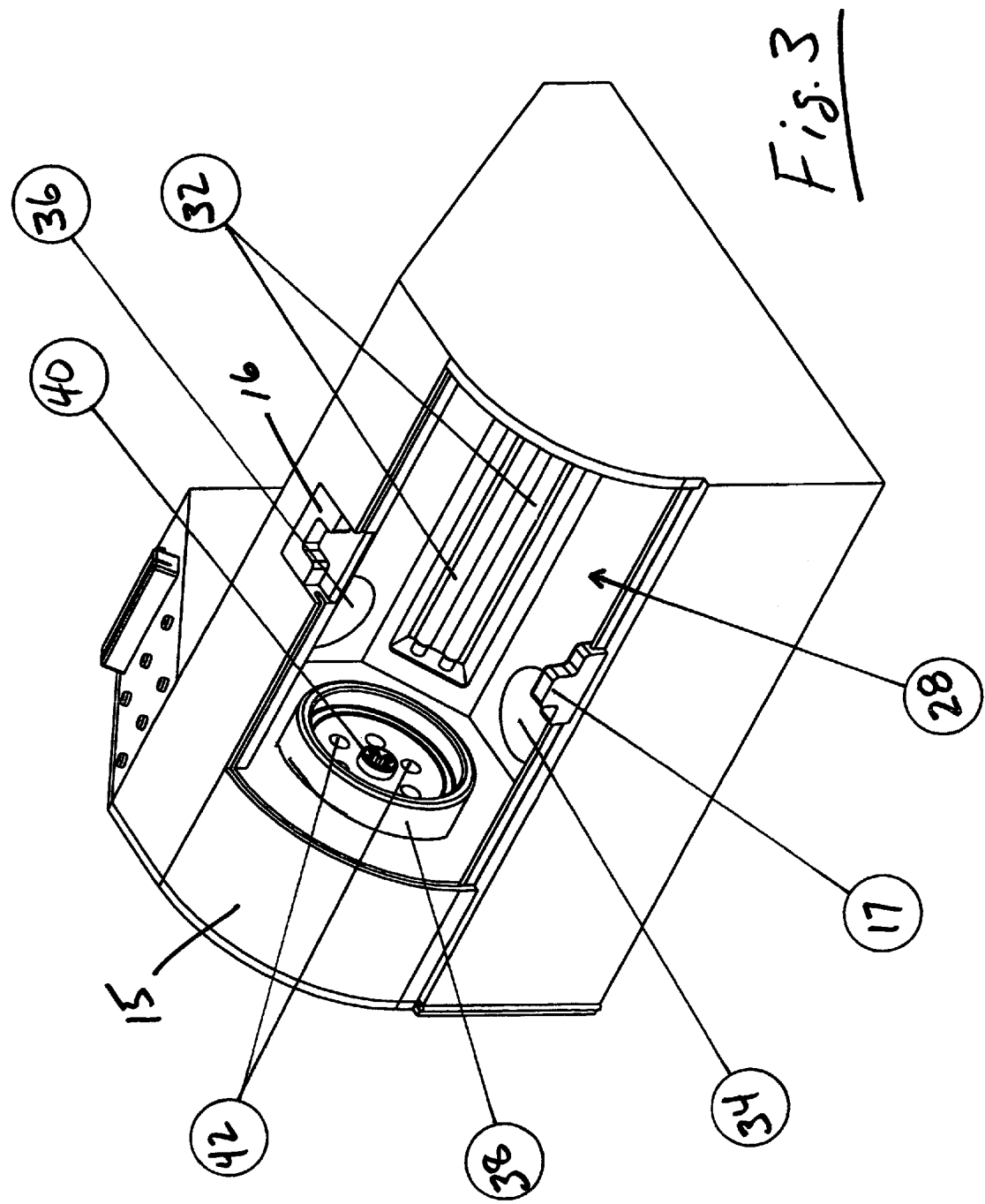
FIG. 3 shows a view of the drive means end of the docking station chamber process area.
Figure 4:
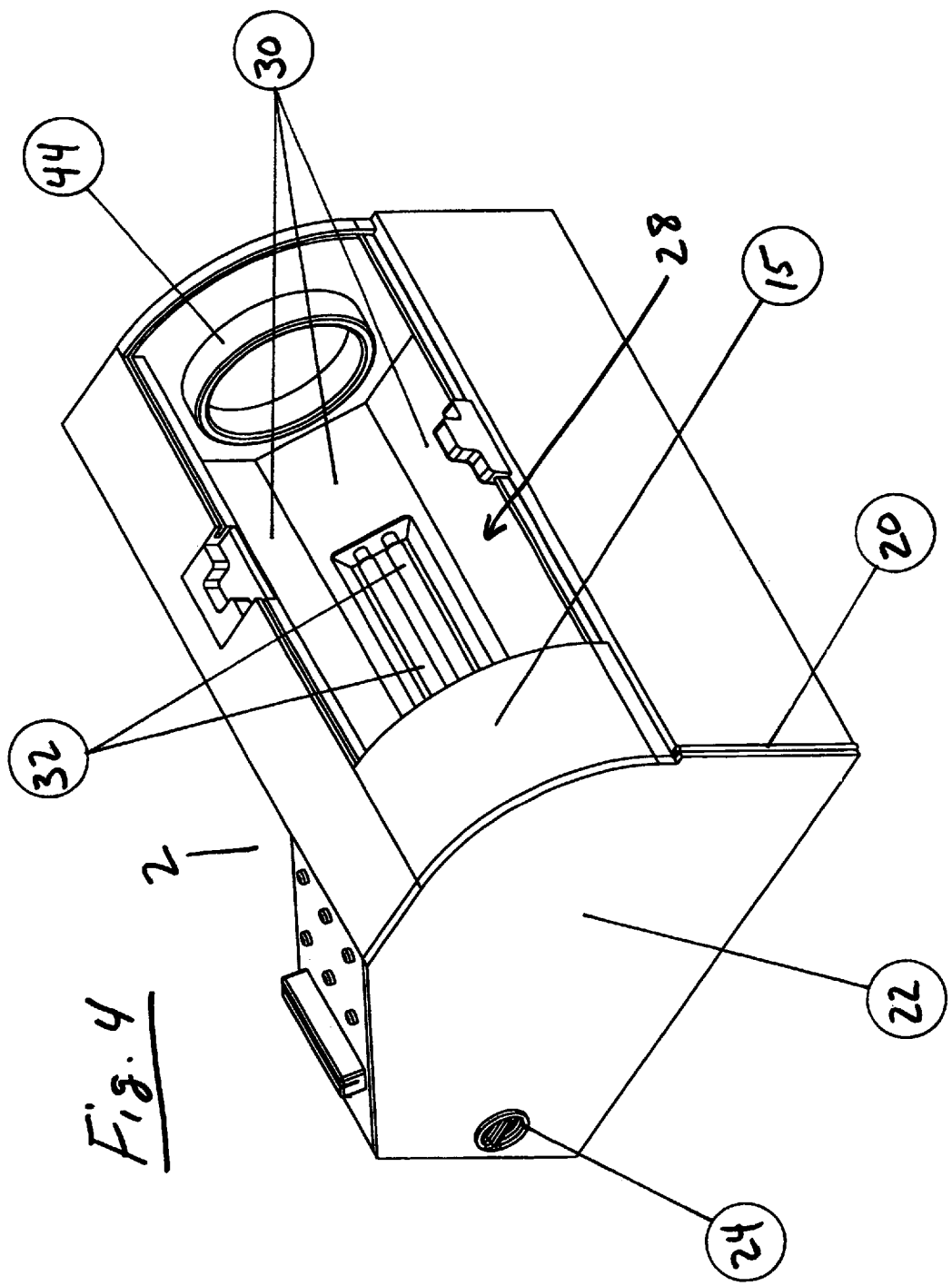
FIG. 4 shows a view of the tailstock end of the docking station chamber process area.

FIGS. 3 and 4 also show the chamber process area 28 having a horizontally mounted magnetic coating mixer drive unit 34, a vertically mounted magnetic coating mixer drive unit 36 (one or both drive units 34, 36 may be present) and a computer controlled docking station drive head 38 for rotating various styles of medical device coating chambers for coating processes. Drive head 38 includes a drive socket 40, for engaging a cylindrical-style chamber mixing drive knob to spin the mixer, and a plurality of introduction ports 42 (six shown) which match those in a coating chamber and allow the docking station to automatically introduce pressure, special gases, and/or other elements into the chamber before, during, and/or after a coating is applied to a medical device. Docking station chassis 15 houses drive motors, electronics, etc. Drive head 38 and drive socket 40 may both be driven by a single motor or may each be driven by a separate motor. A coating chamber supporting tailstock 44 is also included as shown in FIG. 4.

Figure 5:
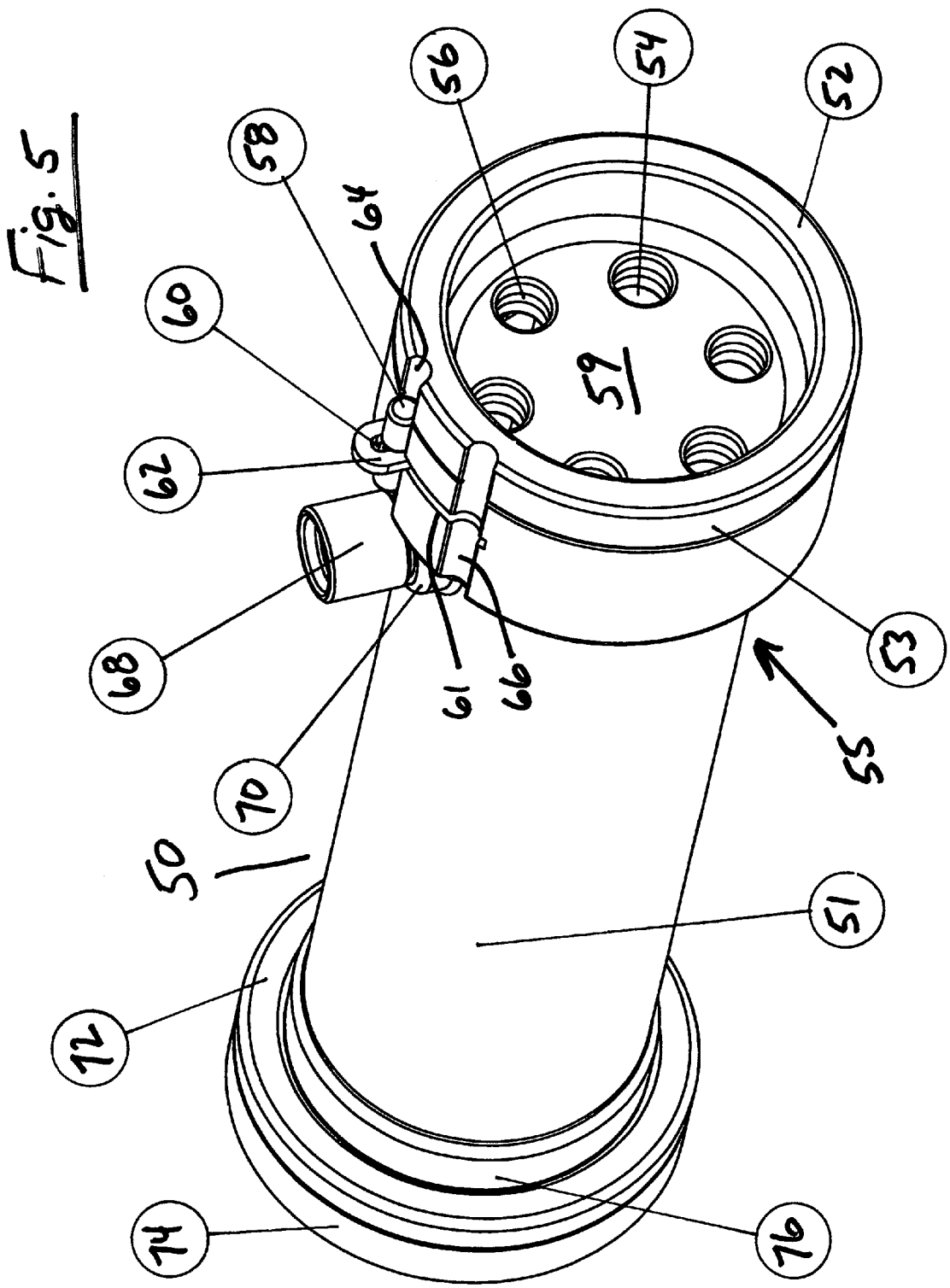
FIG. 5 illustrates a cylindrical-shaped device coating chamber viewed from a coating process end.

FIG. 5 illustrates a cylindrical-shaped device coating chamber 50 (viewed from a coating process end portion 55) which is positionable in a docking station 2 (FIGS. 3 and 4). The coating chamber 50 comprises a chamber cylinder 51 having at one end thereof a support cover 52 with an area of outside diameter 53 of the support cover 52 having a bayonet-style attachment mechanism (not shown), or other positive-attachment means, which is configured to mate with the drive head 38 of the docking station. Also located at one end of the chamber cylinder 51 are a plurality of introduction ports 54 (six shown) in coating floor 59 for controlling the atmosphere, introducing gases and/or other elements into the coating chamber before, during, and/or after a coating is applied to a medical device.

The coating chamber 50 further includes a rotary door 56 which opens and closes the introduction ports, either automatically or manually, such as with a manual rotary door latch roll 58 which lifts up to be moved from an "open" to a "closed" position and back. Preferably, a manual rotary door latch roll spring 60 is mounted in a rotary door control tab 62 for holding the manual rotary door latch roll 58 against docking station support cover 52 and in the "open position" and "closed position" grooves 64, 66 respectively, when the manual rotary door latch roll 58 is not pulled up/away by pulling on control tab 62 which moves between grooves 64, 66 via slot 61. In FIG. 5, the manual version is shown with the rotary door 56 in the "open" position. Of course, rotary door 56 may be opened and closed by any suitable automatic means. Alternatively, each control port 54 may individually be opened and closed either my manual or automatic means. FIG. 5 also shows the chamber 50 having a filtering pressure limiting vent port cover 68 having internal threads to attach to any filtering pressure limiting vent port, attached via boss 70 to the coating chamber 50, on any style of medical device coating chamber.

The other end of chamber cylinder 51 (mixing process end portion 57) includes a chamber mixer attachment cover 72 which holds a chamber mixer assembly in the mixing end of the chamber cylinder. Attachment cover 72 has internal threads (or other positive-attachment means) which attach it to the chamber cylinder 51 and preferably includes an external bayonet-style attachment mechanism (not shown), or other positive-attachment means, on outside diameter 74 of chamber mixing attachment cover 72 which allows attachment to the drive head 38 of the docking station 2 during a mixing process. Cover 72 may include a large access hole (not shown) to allow manual (or automated) loading and emptying of a chamber mixing basket (FIG. 8).

Both ends of the chamber cylinder 51 have a raised shoulder 76 with external threads (or other positive-attachment means) which engage with internal threads (or other positive-attachment means) of docking station support cover 52 on the coater end of the chamber 50, and with internal threads (or other positive-attachment means) of the chamber mixer attachment cover 72 on the mixer end 57 of the chamber 50.

Figure 6:
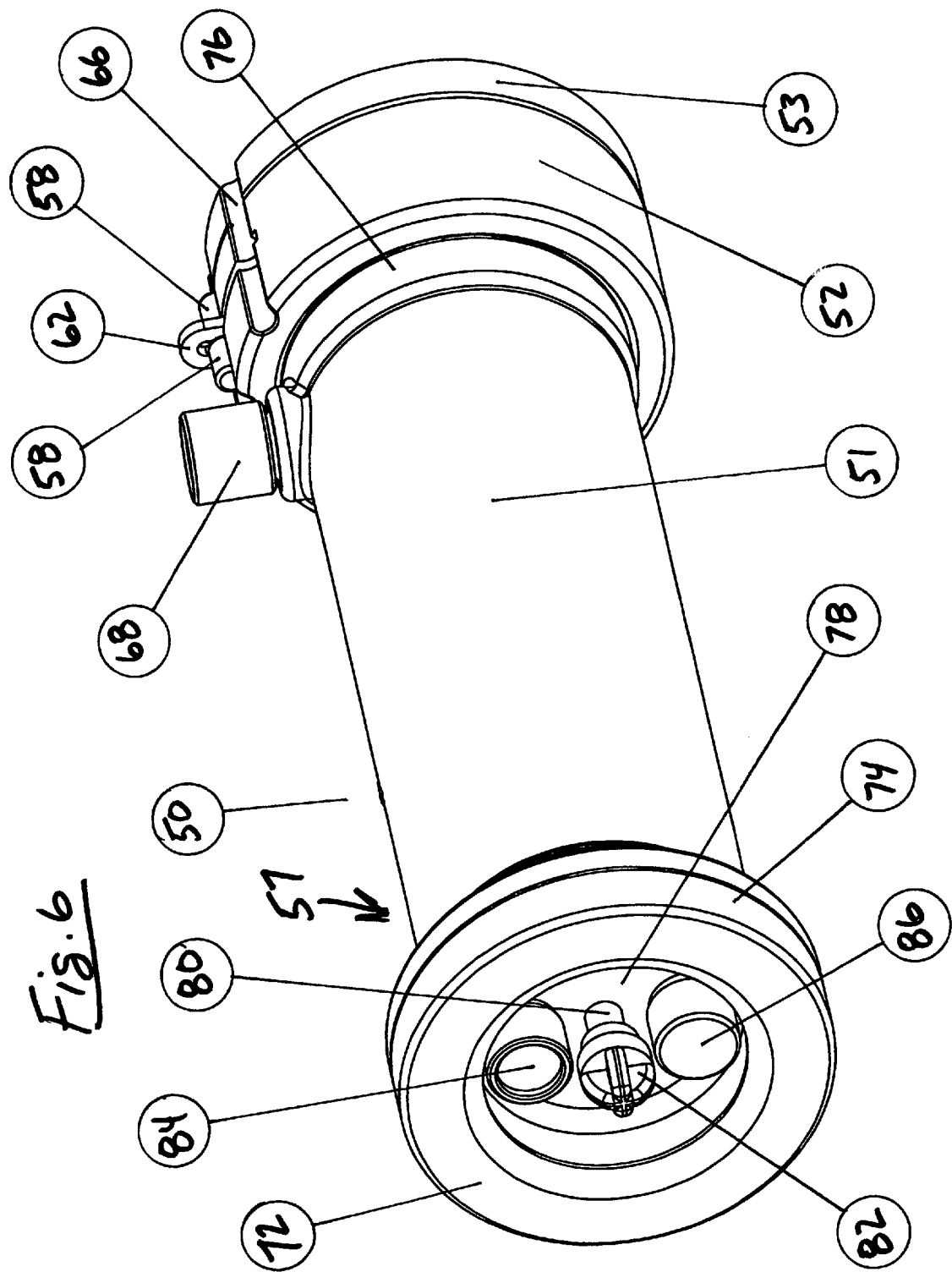
FIG. 6 illustrates a cylindrical-shaped device coating chamber viewed from a mixing process end.
Figure 8:
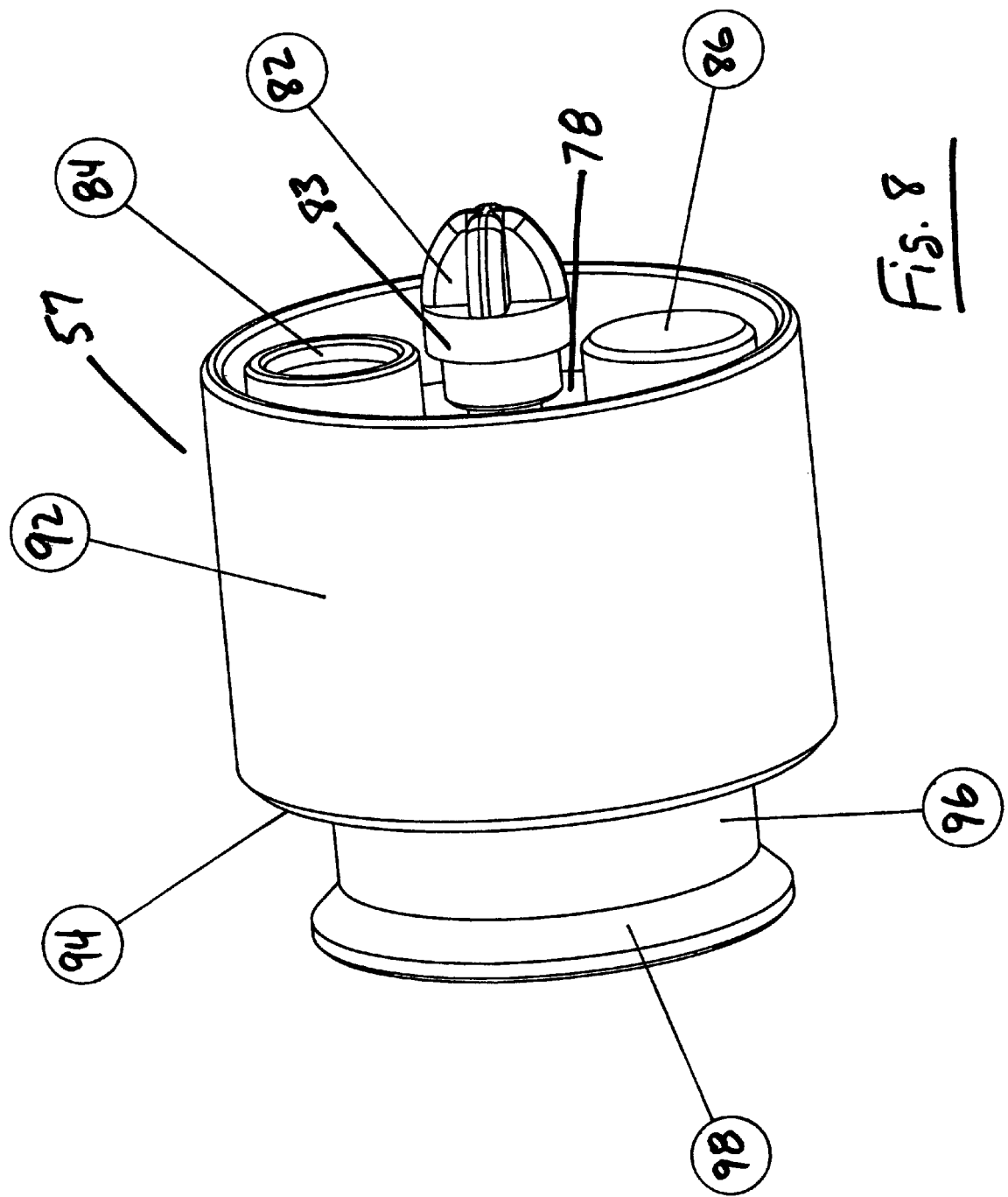
FIG. 8 illustrates a mixing basket portion of a cylindrical-shaped device coating chamber.

FIG. 6 illustrates the cylindrical-shaped device coating chamber 50 viewed from its mixing process end portion 57 which includes a floor 78 of the mixing basket, mixer drive shaft 80 and drive knob 82 which engages drive socket 40 of the docking station 2 (FIG. 3) when the coating chamber 50 is positioned in the docking station 2 for mixing (FIG. 8, discussed below). Mixing process end 57 also preferably includes one or more, preferably two, syringe port covers 84, 86 having internal threads (or other positive attachment) to attach to any syringe port on any coating chamber. In FIG. 6, syringe port cover 84 comprises a needle penetration membrane and syringe port cover 86 is without a needle penetration membrane. Preferably all syringe ports have an electrical contact such that when the cover is replaced with a screw-in (or other positive attachment) syringe, a foil heater and/or temperature sensor in the syringe can receive electrical power and/or computer control.

Figure 7:
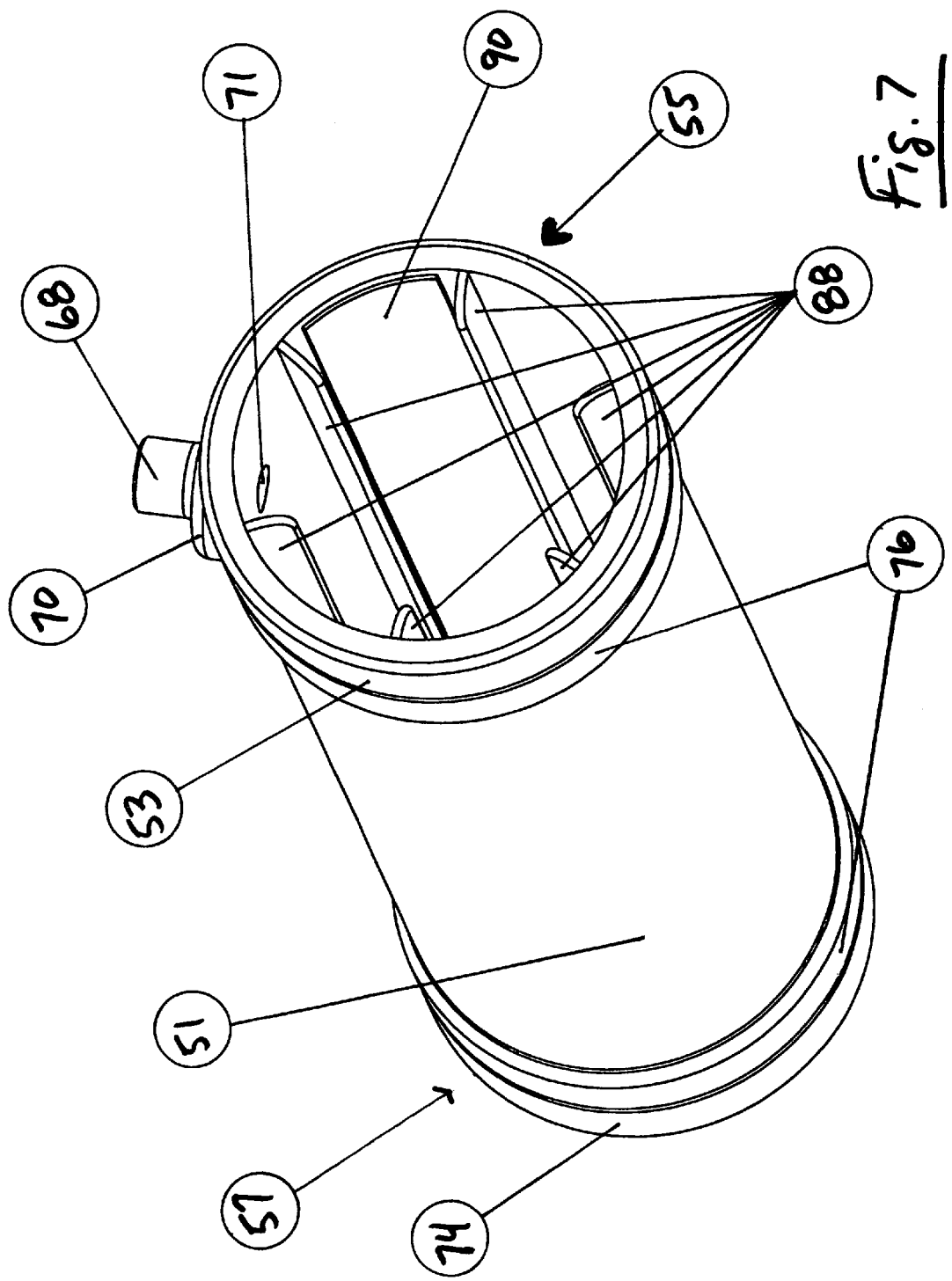
FIG. 7 represents a view into the interior of the coating process end of a cylindrical-shaped device coating chamber.

FIG. 7 represents a view into the interior of the coating process end portion 55 of a chamber cylinder 51. A plurality (six are shown) of coating vanes 88 are spaced, preferably equidistantly, about the interior surface of the coating process end of the chamber cylinder 51. The coating vanes 88 lift a portion of coating mixture from bottom of the chamber as it rotates in the docking station, and the coating mixture bathes, drips or splashes onto a medical device, coating it evenly. A leveling mechanism on the docking station insures the device is coated evenly. A foil heater 90 with temperature sensor (such as the Thermofoil Heater/Sensor manufactured by Minco Products of Minneapolis, Minn.) may also be included. An internal opening 71 communicating with the filtering pressure limiting vent port is also shown.

The mixing process end portion 57 of coating chamber 50 is further illustrated in FIG. 8. A mixing basket is formed by floor 78, basket cylinder 92, shoulder portion 94 and delivery end 96. The mixing basket is held in place in the chamber cylinder 51 by attachment cover 72 (FIG. 6). The inner surface of the basket cylinder 92 includes mixing vanes arranged thereon. Delivery end 96 is opened and closed by a stopper 98, preferably conical in shape, which is actuated by axial movement of mixer drive shaft 80 (FIG. 9) that extends between the drive knob 82 and the stopper 98. Preferably, a spring (not shown) is placed between the floor 78 and the base 83 of the drive knob 82 whereby the force of the spring urges the drive knob 82 away from floor 78 (to the right in FIG. 8) thereby also urging stopper 98 into sealing engagement with the end of delivery end 96. Preferably, the distal portion of delivery end 96 is shaped so as to be complimentary with the form of the stopper 98 (e.g. both are conical) such that an adequate seal is formed upon contact.

Figure 9:
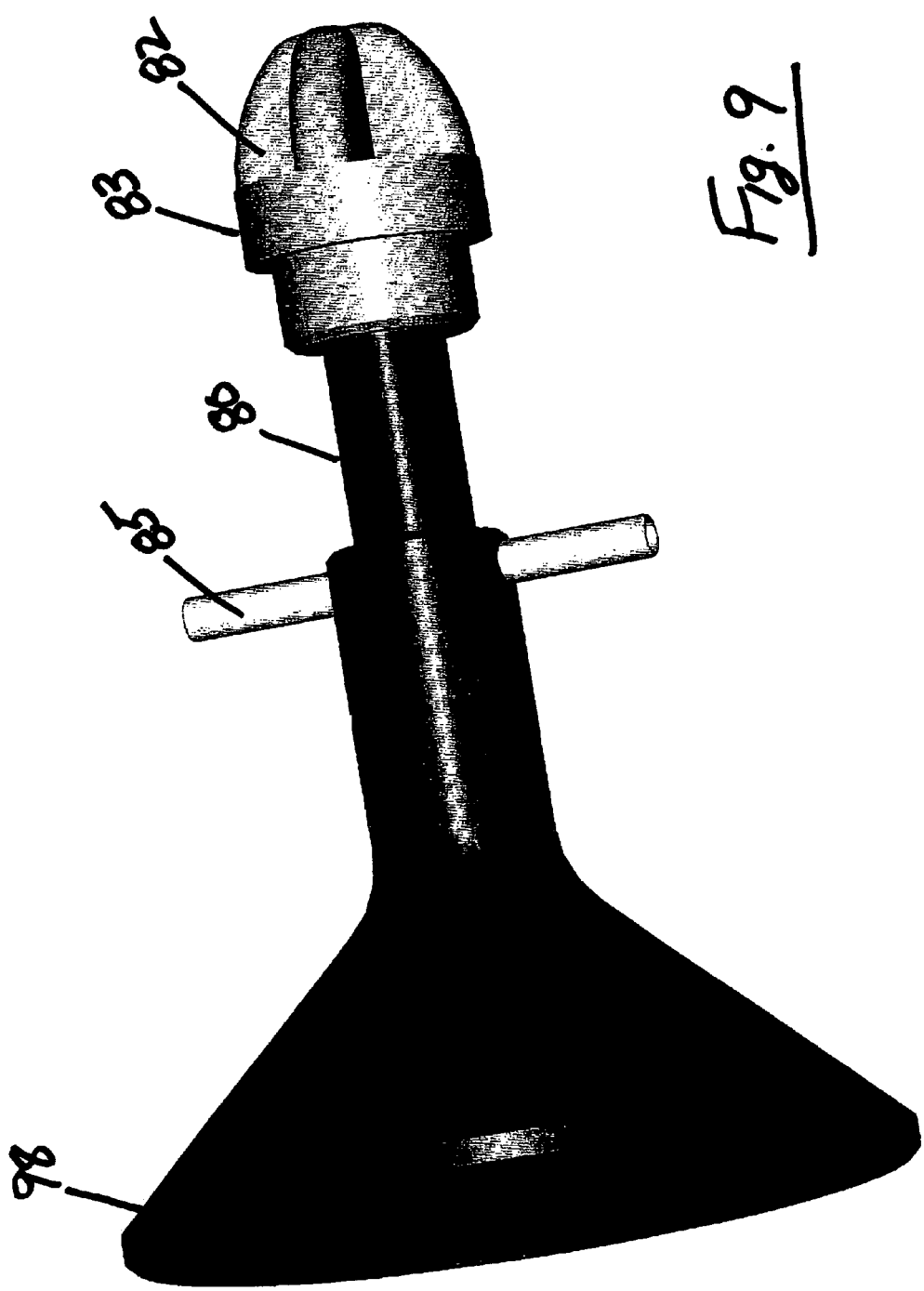
FIG. 9 illustrates a mixing drive shaft and stopper from the mixing basket of FIG. 8.

As seen in FIG. 9, preferably the drive shaft 80 includes a means such as a spring pin 85 that cooperates with the appropriate detent surfaces on the inner surface of floor 78 to control the position of stopper 98. For example, clockwise rotation of drive knob 82 may result in the spring pin 85 encountering a stop surface. Further clockwise rotation of the drive knob 82 thereby results in the rotation of the entire mixing basket as would be the case during the mixing process when the drive knob 82 is engaged with the drive socket 40 of docking station 2. However, the clockwise movement of the spring pin 85 imparts no movement of the drive shaft in the axial direction (the direction on the drive shaft 80) and thus, the stopper 98 remains closed against the delivery end 96 by the action of the spring against the shoulder 83.

On the other hand, counterclockwise rotation of the drive knob 82, such as turning by hand, may result in the spring pin 85 encountering a surface that inwardly tapers (i.e. toward delivery end 96) to a stop surface. Movement of the spring pin 85 along the tapered surface results in the drive shaft 80, and hence the stopper 98, moving to the left in FIG. 8 against the force of the spring, thereby causing the stopper 98 to disengage its seal with delivery end 96 and allow the contents of the mixing basket to flow out and into the coating end 55 of the coating chamber 50.

Figure 10:
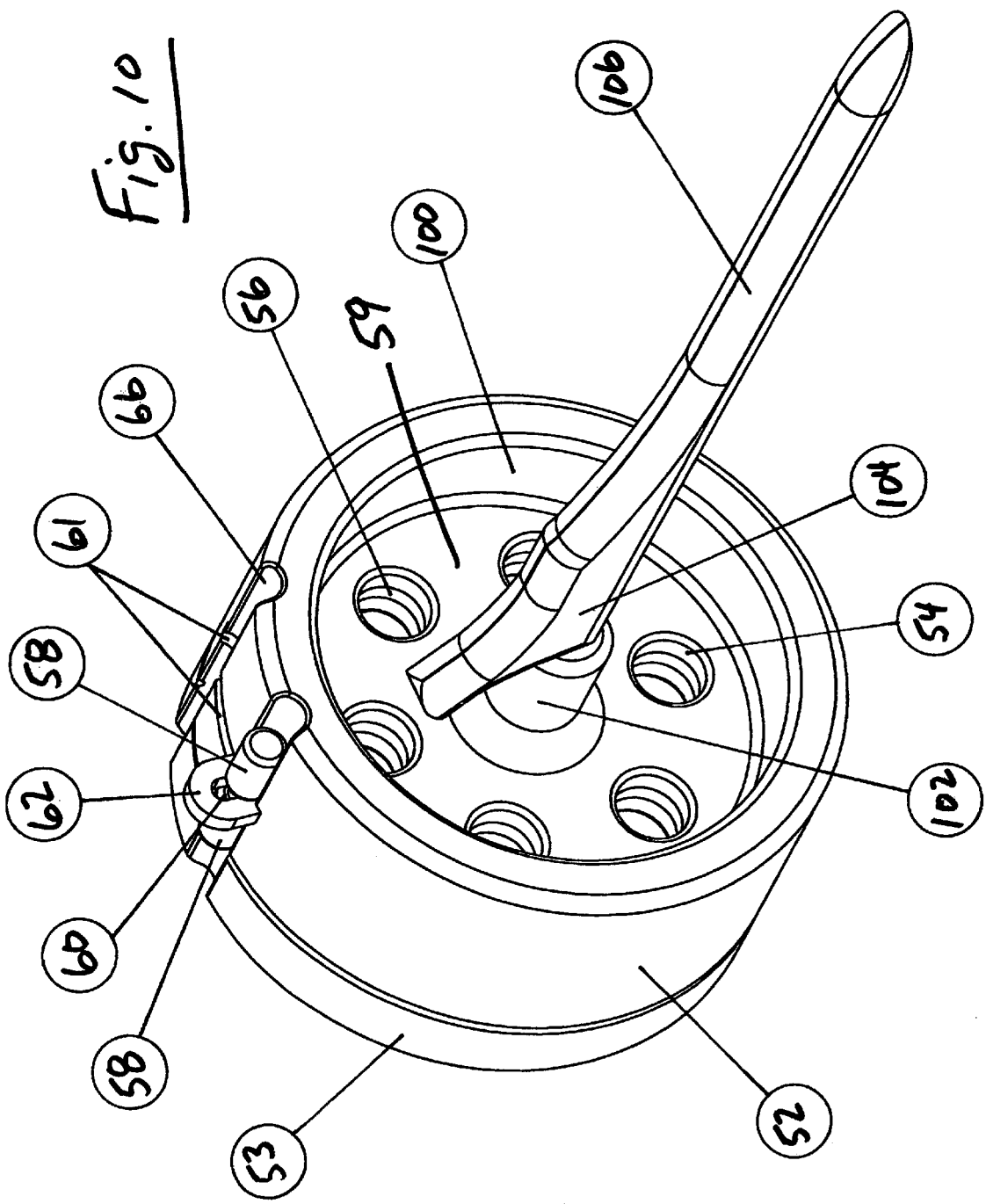
FIG. 10 shows a medical device attached to an interior surface of the coating process end of a cylindrical-shaped device coating chamber.

FIG. 10 shows an interior view of support cover 52, having interior surface 100, which together with the chamber cylinder 51 forms the coating process end 55 (FIG. 5). The interior surface of floor 59 includes a boss 102 and device attachment means 104 which is of a form appropriate for the particular device that is to be coated. In FIG. 10, the device shown is a prosthetic hip 106.

Figure 11:
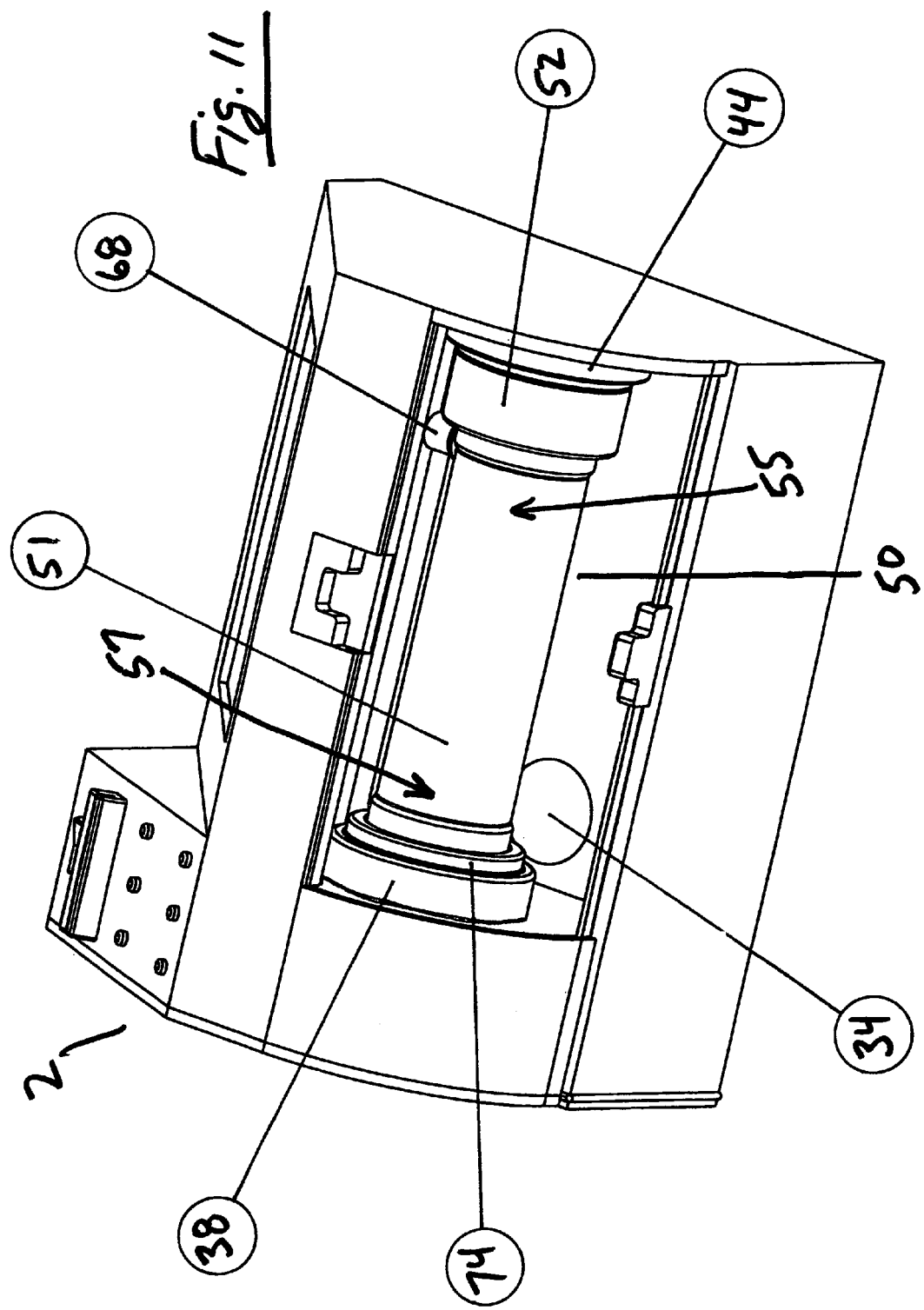
FIG. 11 illustrates a cylindrical-shaped device coating chamber positioned in a docking station for mixing of a coating.

FIG. 11 illustrates a coating chamber 50 positioned in a docking station 2 for mixing to occur in the mixing process end 57 of the coating chamber. The drive knob 82 would be turned in the appropriate direction so that the stopper 98 was closed against delivery end 96 and the desired components would be introduced through one or both ports 84, 86 (FIG. 8). The coating chamber 50 is then positioned in the docking station 2 by inserting the drive knob 82 into drive socket 40 and placing the support cover 52 in tailstock 44. The drive socket 40 is then rotated causing rotation of the coating chamber 50 (and, hence, rotation of the mixing basket) thereby mixing the components previously placed in the mixing basket. The rotational speed and duration are adjustable and are based on the components and mixing requirements.

Once mixing is complete, the coating chamber 50 is removed from the docking station 2 and preferably positioned vertically with the mixing end 57 "up". Drive knob 82 is then rotated as appropriate to open the stopper 98 (as discussed above) thereby resulting in the coating mixture flowing from the mixing basket into the coating process end 55 of the coating chamber 50.

Figure 12:
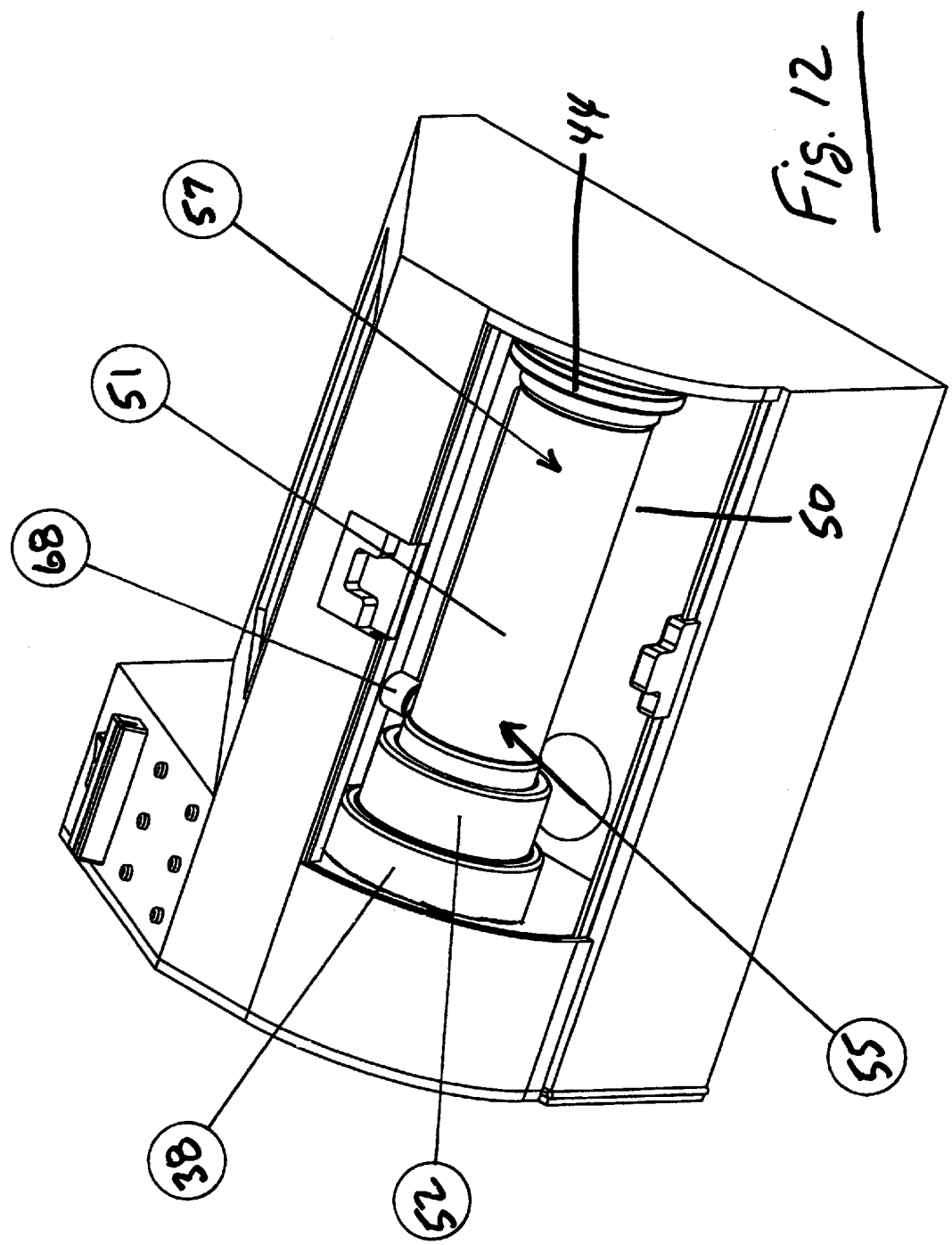
FIG. 12 illustrates a cylindrical-shaped device coating chamber positioned in a docking station for coating a medical device.

After allowing an appropriate amount of time for emptying of the mixing basket, the drive knob 82 is turned in a reverse direction to close the stopper 98 and the coating chamber 50 is returned to the docking station 2 and positioned such that the coating process end portion 55 is engaged with the drive head 38 and mixing process end portion 57 is engaged with tailstock 44 as is shown in FIG. 12. Drive head 38 is rotated, at a desired speed and for a desired time, thereby rotating the coating chamber 50 (and therefore, of course, the coating process end 55). The coating vanes 88 (FIG. 7) lift a portion of coating mixture from bottom of the chamber as it rotates in the docking station 2, and the coating mixture bathes, drips or splashes onto a medical device (such as an artificial hip shown in FIG. 10), coating it evenly. At an appropriate time before, during and/or after coating, introduction ports 54 may be utilized for controlling the atmosphere, introducing gases and/or other elements into the coating chamber.

Additionally, heat (or other energy necessary for curing, for example) may be introduced at a desired time from within the coating process end 55 such as by heater 90 (FIG. 7) or via a source from within the chamber 28 of docking station 2 (FIG. 3). Polymerization can be initiated by the docking station 2 by applying energy (light or microwave), filtered and/or heated air through a chamber port, or electricity to heating foils internal to the chamber. Coating chamber 50 may be fabricated from plastic through which light and/or microwave energy readily passes. Coating chamber 50 may have a medical device installed therein as part of its manufacturing process (hence, medical device is "packaged" in the coating chamber) or a medical device may be installed at the point of coating.

Figure 13:
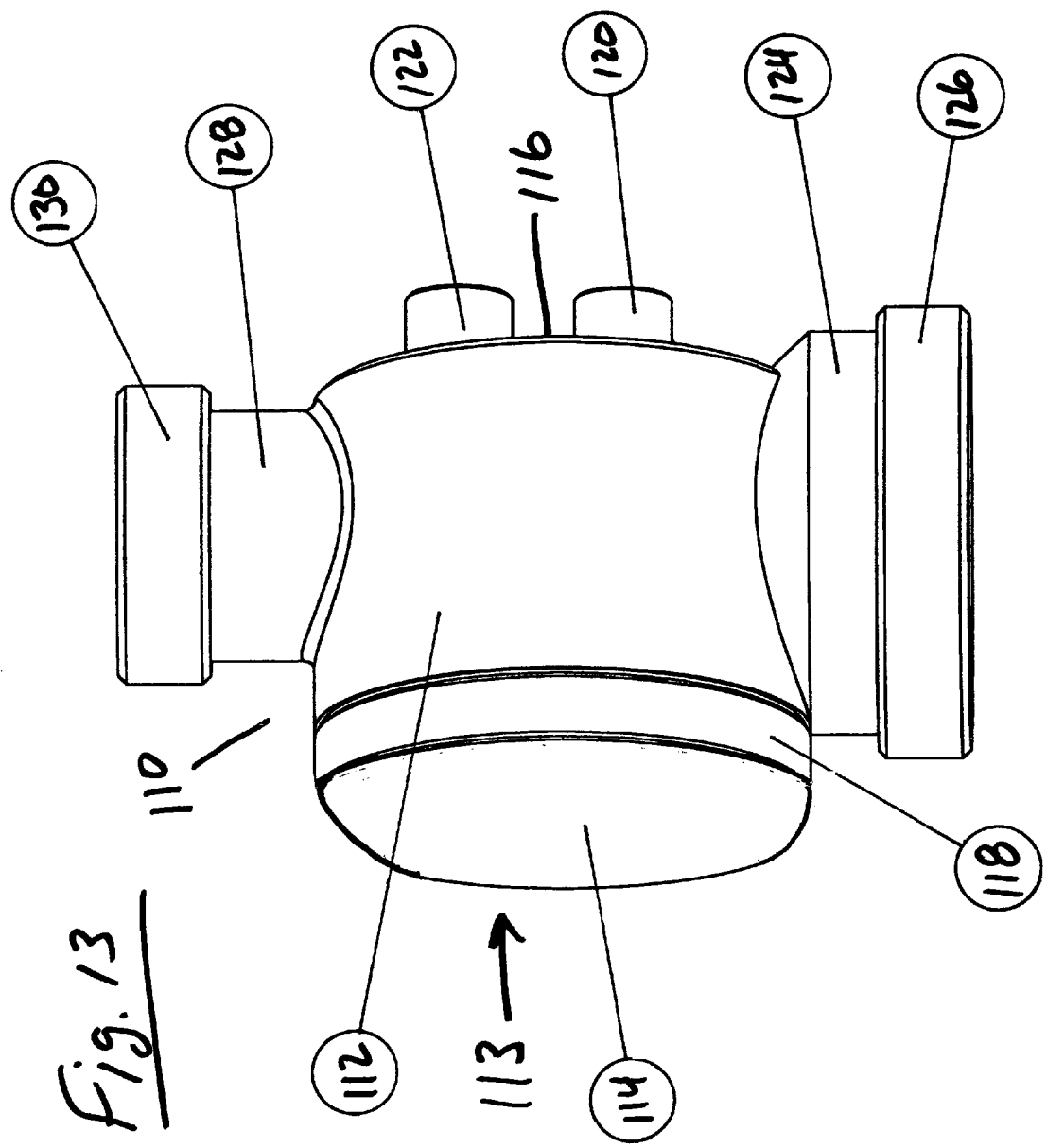
FIG. 13 is a view of a side and drive attachment end of an immersion coating chamber.
Figure 14:
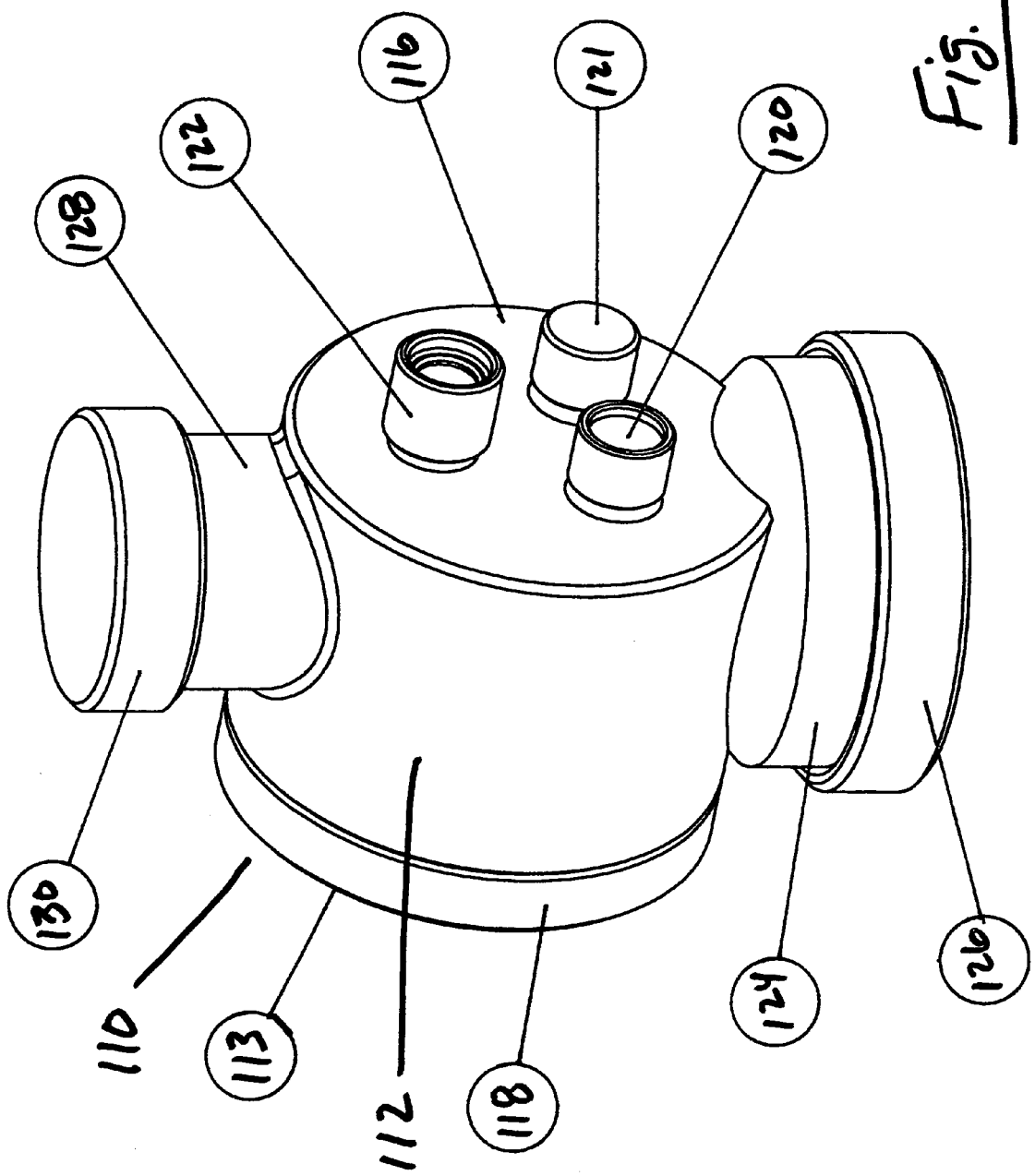
FIG. 14 shows introduction ports of an immersion coating chamber.

While FIGS. 6-12 illustrate a bath, splash or drip type of coating chamber, FIGS. 13 and 14 disclose an immersion coating chamber 110 (which may be fabricated from plastics through which light and/or microwave energy may readily pass) comprising a generally cylindrical shaped main body portion 112 having a first end 113 closed by a wall 114 and a second end closed by a wall 116 which may be removable. Alternatively, first end 113 may be closed by a removable cover which, upon removal, exposes a floor with introduction ports (similar to floor 59 and ports 54 in FIG. 5) to align with ports 42 of the docking station 2 when the coating chamber 110 is positioned in the docking station 2. The area adjacent the first end preferably includes an attachment mechanism 118 such as a bayonet-style attachment mechanism (or other positive-attachment means) for engagement with the drive head 38 of a docking station 2 (FIG. 3).

Wall 116 preferably includes one or more ports with covers (FIG. 14) such as syringe port cover with needle penetration membrane 120, syringe port cover without needle penetration membrane 121 and filtering, pressure-limiting vent port cover 122. All covers have internal threads (or other positive attachment) to attach to any respective port on any device coating chamber. All syringe ports have an electrical contact such that, when the cover is replaced with a screw-in (or other positive attachment) syringe, a foil heater and temperature sensor in the syringe can receive electrical power and/or computer control.

Immersion coating chamber 110 further includes a magnetic drive mixing reservoir portion 124 which houses a magnetic drive mixer. The mixing reservoir 124 is closed by a cover 126 which preferably has internal threads (or other positive-attachment means) and which seals against the face of mixer reservoir 124. Located preferably diametrically opposite of mixing reservoir 124 is an immersion reservoir portion 128 which houses an internal, electrically powered foil heater with temperature sensor. Immersion reservoir 128 is closed by a medical device support cover 130 which preferably has an electrical connection, internal threads (or other positive-attachment means) and which seals against the face of immersion reservoir 128. Medical device support cover 130 supports and positions a medical device (such as a prosthetic heart valve or cardiovascular stent) on a medical device attachment means and preferably includes an internally mounted, electrically powered hotwire coating trimmer.

Figure 15:
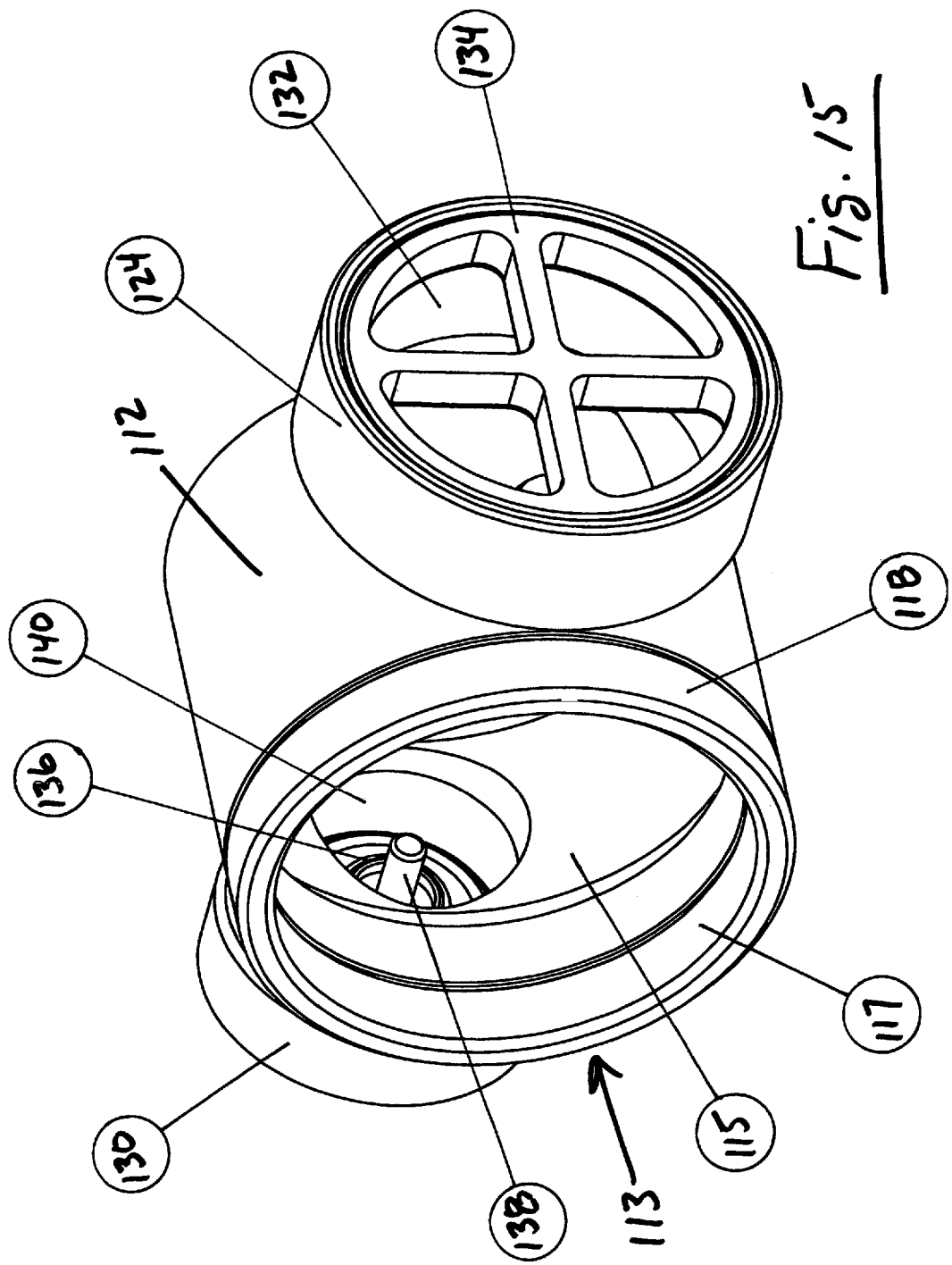
FIG. 15 illustrates the magnetic drive mixer and mixing reservoir of an immersion coating chamber.

In FIG. 15, magnetic drive mixing drive cover 126 is removed to show the interior 132 of the magnetic drive mixing reservoir 124 and the magnetic drive mixer 134. Interior 132 may include a foil heater. Also visible through first end 113 (open, with alternative cover removed and showing location 117 of floor with introduction ports), and through the interior 115 of main body portion 112, is a medical device 136 (prosthetic heart valve shown) mounted to medical device support cover 130 via attachment means 138. An electrically powered and controlled foil heater with temperature sensor 140 is shown positioned in the immersion coating reservoir 128.

Figure 16:
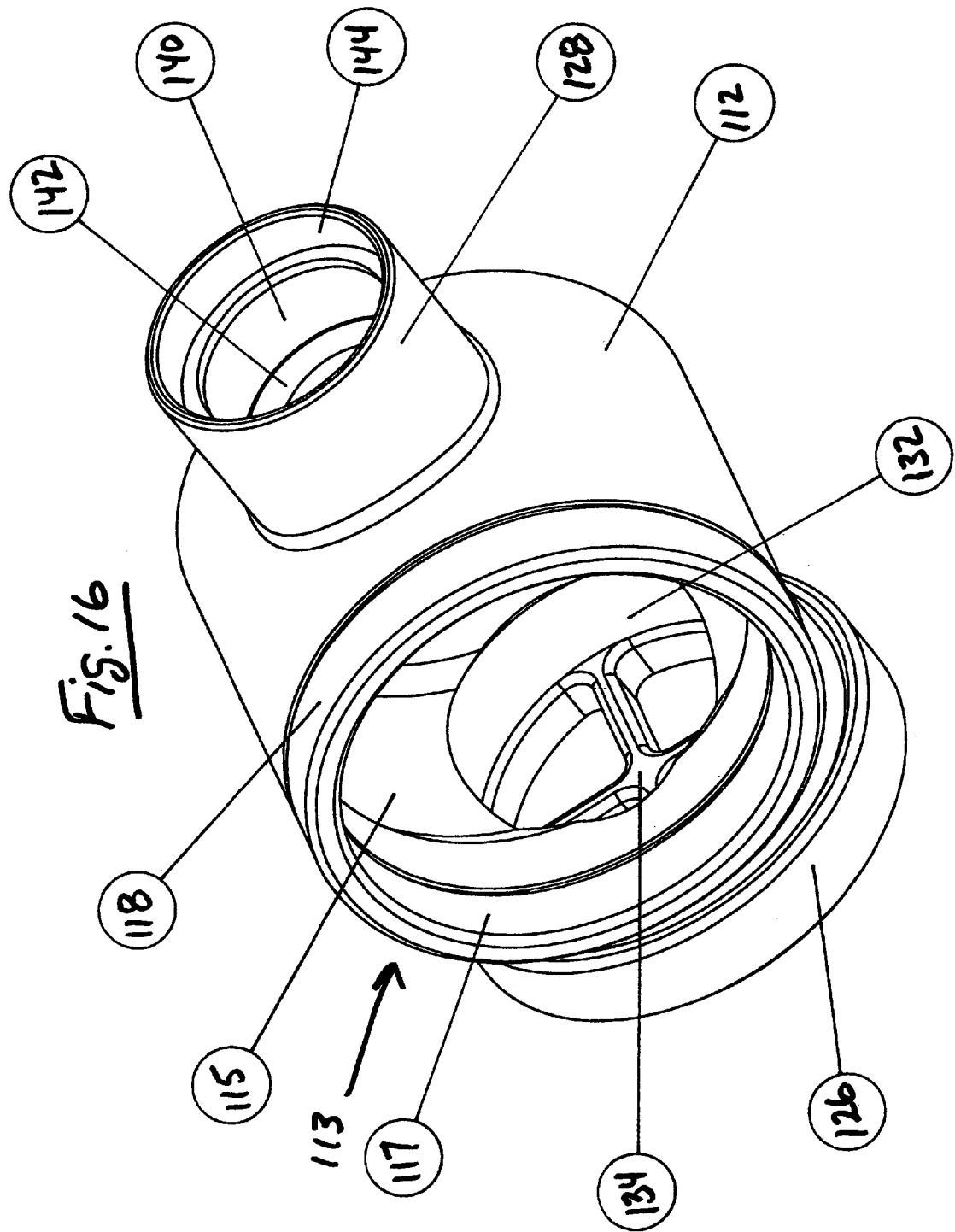
FIG. 16 illustrates the interior of the main body portion and immersion reservoir of an immersion coating chamber.

In FIG. 16, the medical device support cover 130 is removed from the immersion reservoir 128 to show the interior 142 of the immersion reservoir. As appropriate, the inside of the immersion coating reservoir 128 can be configured (such as with a recess and shoulder 144) so as to accommodate a particular medical device support structure and attachment means.

Figure 17:
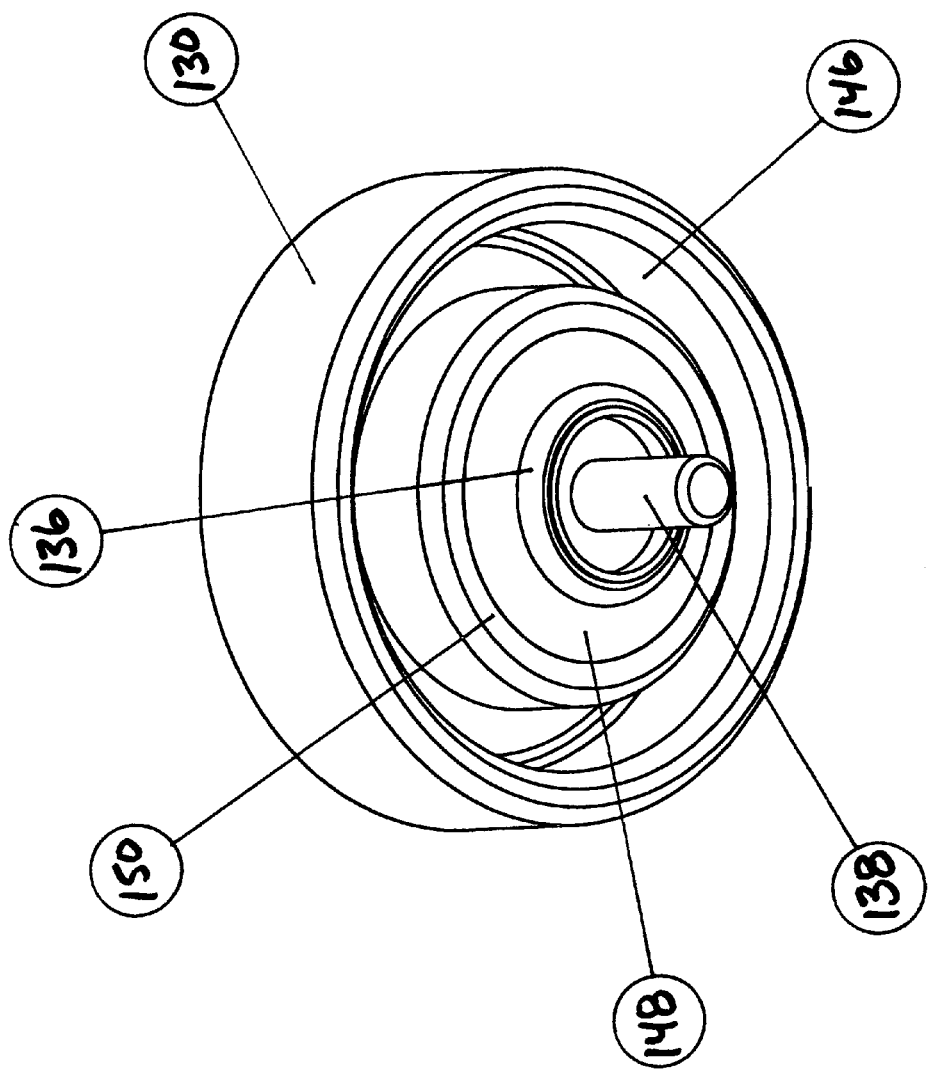
FIG. 17 shows a medical device support cover for attachment to an immersion reservoir of an immersion coating chamber.

FIG. 17 shows a medical device support cover 130 comprising an area of internal threads 146 (or other positive-attachment means) for attachment to immersion reservoir 128. As stated above, support cover 130 includes medical device attachment means 138 to which is attached medical device 136 (prosthetic heart valve shown), an electrically powered and controlled hotwire coating trimmer 148 and a boss 150 for positioning the medical device attachment means 138 and hotwire coating trimmer 148 within the coating reservoir 128. An immersion chamber 110 may have a medical device installed therein as part of the manufacturing process or a medical device may be installed at the point of coating.

Figure 18:
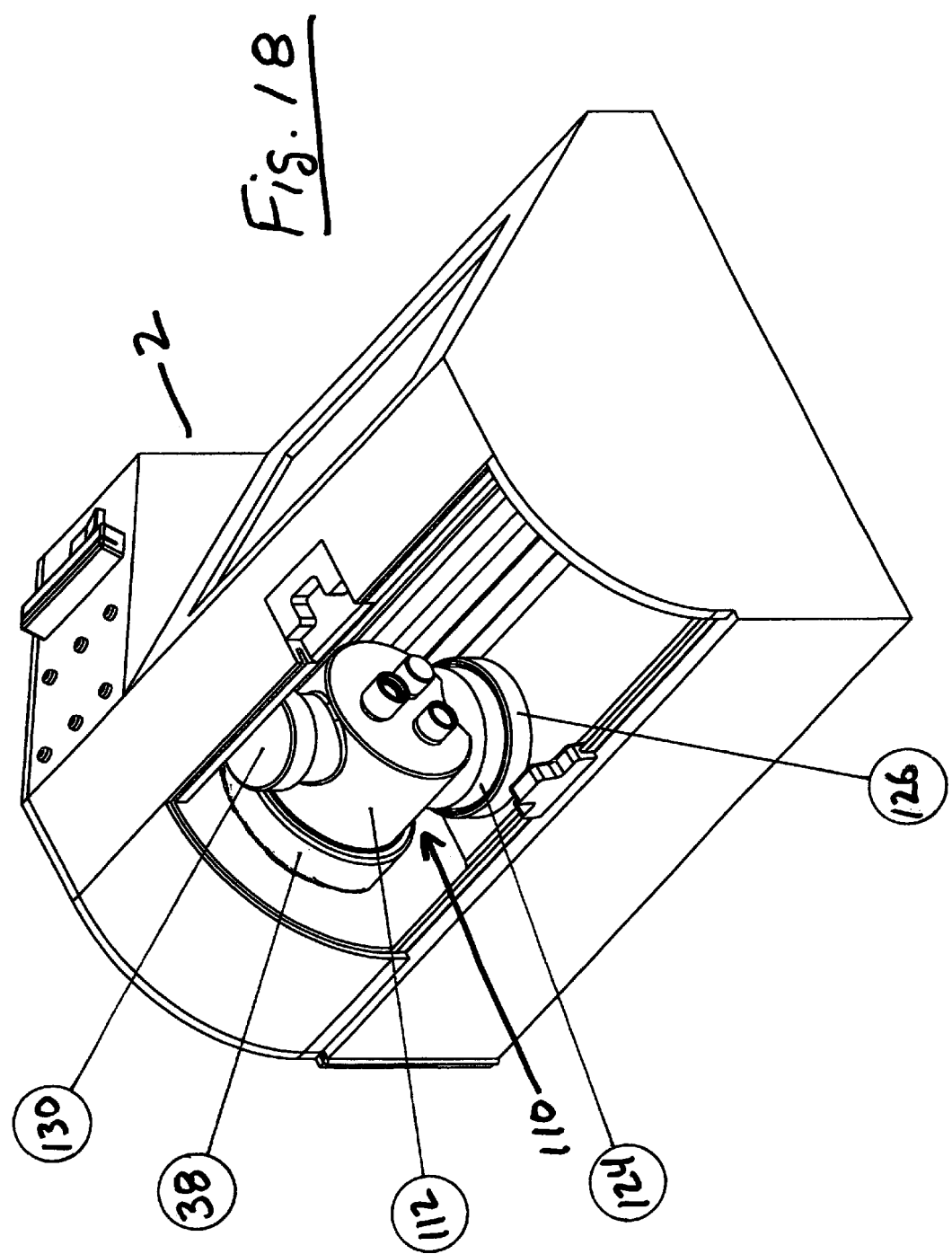
FIG. 18 illustrates an immersion coating chamber positioned in a docking station for mixing of a coating.

FIG. 18 shows the immersion coating chamber 110 positioned in a docking station 2 whereby attachment mechanism 118 is engaged with drive head 38. The coating chamber 110 is oriented by the drive head 38 such that magnetic drive mixing drive cover 126, and hence, magnetic drive mixer 134 are positioned adjacent magnetic coating mixer drive unit 34 (FIG. 3) whereby upon activation of mixer drive unit 34, components such as polymers and/or therapeutic agents previously supplied to the mixing reservoir 124 will be appropriately mixed in accordance with instructions provided to the controller of the docking station 2.

Figure 19:
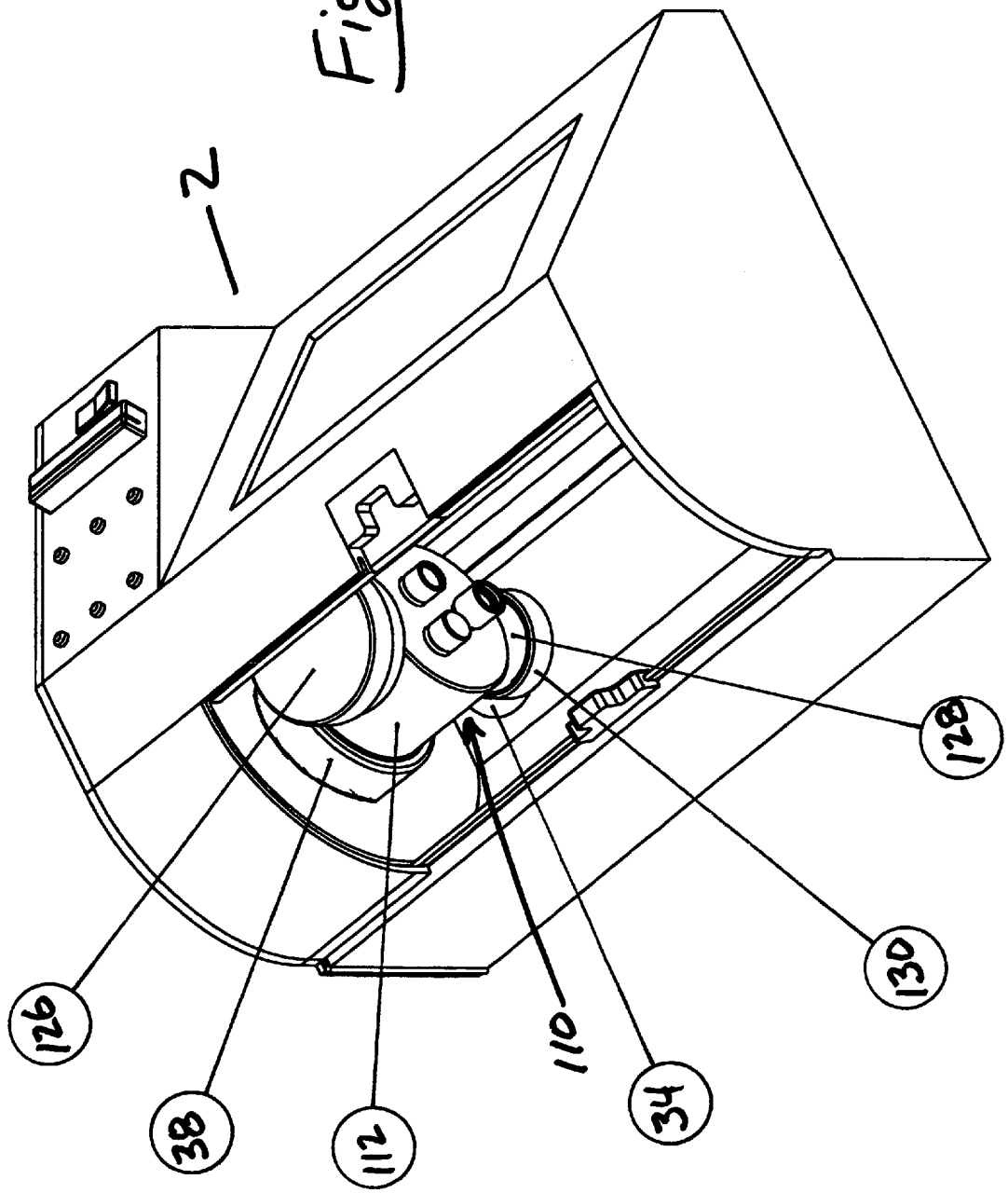
FIG. 19 illustrates an immersion coating chamber positioned in a docking station for coating a medical device.

Upon completion of the mixing, the drive head 38 is activated to rotate the immersion chamber 110 by 180 degrees to the position shown in FIG. 19 wherein the prepared coating residing in mixing reservoir 124 flows into the smaller immersion coating reservoir 128 to immerse the medical device supported on cover 130 in the coating. After a predetermined amount of time, the immersion chamber 110 is again rotated by drive head 38 to a position (such as back to the position shown in FIG. 18) whereby the coating can drain from the medical device and from the immersion coating reservoir 128 back into the mixing reservoir 124 thereby leaving a film on the medical device whose thickness is controlled by the surface tension, density and viscosity of the coating. Additionally, heat (or other energy necessary for curing, for example) may be introduced at a desired time from within the immersion coating reservoir 128 such as by foil heater 140 or via a source from within the chamber 28 of docking station 2 (FIG. 3). After the coating process is complete, the support cover 130 can be removed, providing access to the coated device.

Cured polymer flash adhering to device support can be addressed by the electrically powered and controlled hotwire coating trimmer 148. After the polymer film has been formed and polymerized or cured, the docking station can energize the resistance wire to burn off the polymer film at the support member contact points. Additionally, cured polymer adhering to the chamber and adhering the chamber lid to the body may be addressed by equipping the docking station with a wrench type mechanism (not shown) into which the chamber lid can be inserted to assist the medical personnel in disconnecting the chamber body from the lid.

In its simplest form, an immersion coating chamber may have the shape of a cone, pyramid or trapezoid. The important aspect being that the mixing reservoir is of a size to hold sufficient coating mixture such that upon inverting the immersion chamber, the coating mixture will flow into the coating reservoir and immerse the device to be coated. Of course, it should be understood that if mixing of coating constituents is not necessary, the coating composition may be introduced directly into the coating process portion of a coating chamber (e.g. coating process end portion 57 or immersion coating portion 128).

In operation, the individual operating the docking station 2 and the immersion coating chamber 110 (including an implantable medical device that was attached to cover 130 by the manufacturer, or alternatively, attached to cover 130 at the point of care), following interactive instructions on the touch screen 18 of the docking station 2, would install the immersion chamber in the docking station 2 by attaching the chamber opening 113 to the docking station drive head 38 (FIG. 18) via attachment mechanism 118. Next, the operator would initiate a "coating ingredient loading cycle", and the docking station 2 would position the immersion chamber 110 so that its magnetic coating mixer 134 (and mixing reservoir 124) is down and its medical device coating reservoir 128 is up. Next, the operator would utilize the syringe ports 120 and/or 121 to deposit a pre-determined set of coating ingredients into the coating chamber. Following that, the docking station rollup door would need to be closed to then initiate the "coating mix cycle" by the magnetic mixer. When mixing is complete, the docking station may pause until the operator has initiated the "medical device coating cycle", during which docking station drive head 38 would rotate the coating chamber 180 degrees to immersion-coat the implantable medical device (FIG. 19). The coating chamber 110 would then be rotated back to the original position and, possibly, the hot-wire coating trimmer may be activated. After the coating is cured, the docking station 2 may direct the rotation of the immersion coating chamber about 45 degrees so that the support cover 130 with the coated medical device attached could be removed from the immersion coating chamber, and so that the coated medical device could then be removed from the cover and implanted.

EXAMPLE 1

Artificial Knee or Hip (An Orthopedic Implant)

The device is coated at the point of manufacture with Hydroxyapatite (HAp), a naturally derived material that makes up bone mineral and the matrix of teeth. Hydroxyapatite is biocompatible and can be coated onto the surface of a medical device with porous properties that support the absorption of therapeutic agents and their subsequent delivery after the device is implanted. The porous Hydroxyapatite coated medical device is sterilized and delivered to the point of care in the chamber. An alternative bonding/linking technology for this example is to coat the device at the point of manufacture with a linker technology which bond functional peptides to biological materials and to synthetic materials. Linker technology is available from, for example, Affinergy Inc., Research Triangle Park, N.C. A therapeutic protein to initiate a biological function related to the bone is added through the injection ports, mixed thoroughly in the chamber if required, heated to reduce their viscosity if required after which the chamber rotates and bathes the device in therapeutic agent for sufficient time, controlled by the docking station, such that the therapeutic agent is absorbed by the Hydroxyapatite coating or linked to the functional peptide. The docking station can then stop rotation and bathing of the device, allow for sufficient time for the device to drain, blow off excess therapeutic agent and dry the surface if desired, having maintained a sterile atmosphere throughout the process. This process allows for the delivery of a therapeutic protein that may not have survived sterilization and would have limited shelf life had it been applied at the point of manufacture.

EXAMPLE 2

Heart Valve

A prosthetic heart valve is delivered, sterile, in an immersion chamber. At the point of care, an in vivo biocompatible and biodegradable polymer, such as one produced from star shaped polylactide containing an ethoxylate core and functionalized with acrylate and methacrylate pendant groups, is injected into the chamber at the point of care. This polymer system is selected because of the ability to activate it with light and change from a soft structure to a strong mechanical structure that can withstand the flow and pressure of blood in the heart. A therapeutic agent, such as an antimicrobial peptide is added either in conjunction and mixed with the polymer or in a separate step. The docking station then controls a process for mixing the polymer and therapeutic agent, inverts the chamber through rotation such that the unmasked heart valve suture ring is saturated with the polymer/therapeutic agent solution. After allowing sufficient time for absorption into the suture ring and/or the coating of the suture ring surface, the docking station then inverts the chamber such that the heart valve now drains of excess coating. After sufficient time for complete drainage, the docking station turns on the light source for a timed cure of the polymer then energizes the hot wire at the implantable device attachment points to burn of excess flash coating. The device has now been coated with an in vivo biodegradable coating containing a protein based therapeutic agent.

EXAMPLE 3

Cardiovascular Stent

A cardiovascular stent is coated at the point of manufacture with Hydroxyapatite or a linker technology such as that offered by Affinergy, Inc. of Research Triangle Park, N.C., for example, and delivered to the point of care sterile in the shipping/coating chamber. At the point of care, a therapeutic agent to inhibit restenosis such as the VEGF receptor KDR/flk-1 is added through the injection port of the chamber. Therapeutic agents such as KDR/flk-1 have advantages over proliferation inhibiting drugs in that peptides and proteins such as KDR/flk-1 prevent restenosis by accelerating the re-establishment of the proliferation down-regulating endothelial tissue. Sterilization and shelf life limitations make difficult the application of peptides, proteins and biological therapeutic agents at the point of manufacture. The chamber containing the therapeutic agent and the stent is inserted into the docking station which, by reading bar codes and/or imbedded chips, confirms the correct stent, coating and therapeutic agent then inverts the chamber through rotation such that the hydroxyapatite stent coating or the functional peptide linker is saturated with the therapeutic agent. After allowing sufficient time for absorption into the stent coating or attachment to the functional peptide linker, the docking station then inverts the chamber such that the stent now drains of excess coating.

EXAMPLE 4

Heart Valve

A heart valve is coated with functional peptide linker such as that developed by Affinergy, Inc. of Research Triangle Park, N.C., at the point of manufacture. Affinergy's functional peptide linker utilizes two custom peptides linked together, one of which can selectively bind to synthetic materials such as the sewing ring material (Dacron) of the heart valve and the other to a biological material (biologic). The coated heart valve is sterilized and delivered to the point of care.

While pre-coating a medical device prior to application of a final coating of a polymer and/or therapeutic agent has been discussed above with respect to linking, binding and absorbing types of pre-coatings, adsorbing types of pre-coatings, such as ion attracting types of coatings, are also contemplated as pre-coating compositions.

At the point of care, a biological therapeutic agent which accelerates or stimulates the natural healing process and the production of endothelial cells may be added. Examples of biologics for accelerating the formation or collection of endothelial cells include an antibody specific to the antigen cells that are in the blood which captures the patients circulating endothelial progenitor cells in order to accelerate the natural healing process. This antibody is available from Bio-Invent International AB of Lund, Sweden and has been developed for cardiovascular stents by Orbus Medical Technology of Fort Lauderdale, Fla. A second example of a Biologic which can be attached to the heart valve at the point of care, using the previous described peptide linker technology is the VEGF receptor KDR/flk-1 which is rate-limiting for a fast regeneration of the endothelium resulting in an acceleration of the natural healing process.

In this example of a point of care applied biologic, the invention device described for applying a coating and therapeutic agent at the point of care is not needed as the biologic can be attached to the peptide linker at the point of care by means such as direct immersion into a container for a short non critical period of time The present invention also contemplates a chamber of any shape which utilizes atomized liquid or spray droplets to coat a device. The atomized particles can be produced by an ultrasound transducer in the base of a chamber, or in the docking station and acoustically coupled to the chamber or by ultrasound atomizing nozzles, such as those manufactured by Sono-Tek Corporation in Milton, N.Y., in the chamber or in the docking station. Atomization can be accomplished in a contained atmosphere, thereby eliminating the hazard of airborne polymer and therapeutic agents. Spray droplets can be produced by pressurized gas delivering polymer and/or therapeutic agents to spray nozzles distributed throughout the chamber. A filter and/or filter collection chamber on the chamber collects the polymer and therapeutic agent, thus preventing their release into the atmosphere.

Polymer and/or therapeutic agents can be applied as atomized or spray droplets in specific metered amounts (such as with equipment supplied by Sono-Tek) or in excess whereby the excess is allowed to drain off the device, in which case, the coating thickness and drug delivery are controlled by the solution viscosity, density, surface tension and the chamber internal temperature.

Polymer and/or therapeutic agents can be conveniently added to a chamber at the point of care utilizing pre-filled syringes. A syringe with multiple barrels of the same or different diameters can be pre-filled with the polymer and therapeutic agent to be added at the point of care to the chamber. If a chemical reaction is required to cure the polymer, a three-chamber syringe can be provided with two chambers dedicated to the polymer system and the third to the therapeutic agent. If a chemical reaction is not required to cure the polymer, a two chamber syringe can be provided with one chamber dedicated to the polymer and one to the therapeutic agent. The barrel(s) dedicated to the polymers can be equipped with a one-way check valve so that the user may draw up the therapeutic agent into that dedicated chamber only. The syringe may have an in-line mixing feature at the tip, mixing the contents of all barrels as the syringe plunger is depressed. The syringe may be equipped with an external heating foil and thermistor to preheat the contents that will be activated and controlled when placed in the docking station.

The docking station of the present invention addresses quality control and regulatory concerns of coating an implantable medical device at the point of care by delivering a reproducible process that is independent of user training or skill. The docking station capabilities including one or more of the following:
- provides a controlled process for coating an implantable medical device at the point of care, independent of skill level or training of the attending medical personnel;
- reads barcodes, confirms drug, devices and process;
- has the means to provide a level plane for even distribution of coating;
- mixing: the docking station can include a mixer;
- rotation: chamber rotation insures even coverage of the device;
- temperature control within the chamber and of the syringe containing the polymer and/or therapeutic agent;
- atmosphere control—gas, pressure and/or vacuum if required;
- times and controls specific processes;
- indicates stage of process and when cycles are complete;
- coats a device by immersion (rotates chamber 180 degrees), bath with rotation (such as 350 degree reversing rotation) for uniformity, and/or atomizing spray heads;
- delivers and controls energy to cure the polymer/therapeutic agent coating by light, microwave and/or heat.

In addition, the coating chamber has capabilities which include one or more of the following:
- provides a sterile, robust container for shipping and inventory;
- provides an environmentally controlled chamber for coating a sterile implantable medical device with a polymer and/or therapeutic agent at the point of care;
- provides a means of distributing the coating uniformly over the surface of the device by immersion, bathing the device and/or spray;
- provides a means of curing a polymer under controlled atmosphere (vacuum or pressure, gas) and energy (heat, light and/or microwave).

While the invention has been described with reference to preferred embodiments it is to be understood that the invention is not limited to the particulars thereof. The present invention is intended to include modifications which would be apparent to those skilled in the art to which the subject matter pertains without deviating from the spirit and scope of the appended claims.

What is claimed is:

1. An apparatus for coating a medical implant device with at least one of a polymer and therapeutic agent at a location of patient care, said apparatus comprising:
   a chamber having a coating portion in which said device is positioned and in which said at least one of a polymer and therapeutic agent is applied to said device, said coating portion including an attachment means for positioning said device for coating,
   a docking station in which said chamber is positionable therein and removable therefrom, said docking station including means to control at least one of the rotation and rotational positioning of said chamber, said docking station further including means to control one or more coating process conditions within said coating portion,
   wherein said coating portion further includes a hotwire coating trimmer.

2. The apparatus of claim 1 wherein said chamber further includes a mixing portion into which components of said at least one of a polymer and therapeutic agent are introduced for mixing to form said at least one of a polymer and therapeutic agent, said mixing portion being in controlled communication with said coating portion.

3. The apparatus of claim 1 wherein said apparatus comprises a drive means to rotate said chamber at a predetermined speed and by a predetermined angular amount.

4. The apparatus of claim 2 including drive means to effect mixing in said mixing portion.

5. The apparatus of claim 4 wherein said drive means comprises a magnetic drive unit.

6. The apparatus of claim 4 wherein said drive means comprises a drive socket for engagement with a mixer drive shaft in said mixing portion.

7. The apparatus of claim 1 including at least one of means to read, store, review and integrate information regarding one or more of the medical implant device, the polymer and the therapeutic agent; said apparatus further including means to control at least one of the mechanics, quality and documentation of the coating process.

8. The apparatus of claim 1 wherein said chamber is removable from said apparatus.

9. The apparatus of claim 1 wherein said medical implant device to be coated includes at least one of a binding, linking, absorbing and adsorbing pre-coating thereon.

10. The apparatus of claim 9 wherein the pre-coating comprises a functional peptide linker or hydroxyapatite.

11. The apparatus of claim 1 wherein said chamber includes a plurality of introduction ports.

12. The apparatus of claim 2 including one or more introduction ports positioned to communicate with one or more introduction ports in said at least one of said coating portion and said mixing portion.

13. The apparatus of claim 1 wherein said chamber is generally cylindrical in shape, the cylindrical chamber being positionable generally horizontal in said apparatus and being rotatable about an axis extending in the horizontal direction to effect a bathing or splashing of the said at least one of a polymer and therapeutic agent on the medical implant device in the coating chamber.

14. The apparatus of claim 2 wherein said chamber comprises a generally horizontal axis of rotation when positioned in said apparatus and wherein said mixing portion and said coating portion are attached to and in communication with said chamber and are oriented perpendicular to said horizontal axis.

15. The apparatus of claim 14 wherein said mixing portion and said coating portion are diametrically opposed to one another.

16. The apparatus of claim 14 wherein said mixing portion is positioned at a lower orientation than said coating portion for mixing the components of said at least one of a polymer and therapeutic agent, and wherein said apparatus is operable to rotate said chamber by a predetermined amount whereby said coating portion is positioned at a lower orientation than said mixing portion thereby effecting a flow of said at least one of a polymer and therapeutic agent into said coating portion to immerse and coat a medical implant device supported in said coating portion.

17. The apparatus of claim 2 wherein one or both of said coating portion and said mixing portion includes a heating means.

18. The apparatus of claim 13 wherein said coating portion includes a plurality of coating vanes.

19. The apparatus of claim 2 wherein said mixing portion comprises a mixing basket having an inner end portion operable to open to deliver said at least one of a polymer and therapeutic agent into the coating portion.

20. The apparatus of claim 1 further comprising a source of light and/or microwave energy for penetrating said chamber to cure a coating on a medical implant device.

21. The apparatus of claim 11 wherein said apparatus controls the atmosphere of the coating chamber and comprises a source of at least one a predetermined type of gas, a gas under a desired pressure, or a vacuum which can be introduced into said chamber via the introduction ports.

22. An apparatus for coating a medical implant device with at least one of a polymer and therapeutic agent at a location of patient care, said apparatus comprising:
   a chamber having a coating portion in which said device is positioned and in which said at least one of a polymer and therapeutic agent is applied to said device, said coating portion including an attachment means for positioning said device for coating,
   a docking station in which said chamber is positionable therein and removable therefrom, said docking station including means to control at least one of the rotation and rotational positioning of said chamber, said docking station further including means to control one or more coating process conditions within said coating portion,
   wherein said chamber further includes a mixing portion into which components of said at least one of a polymer and therapeutic agent are introduced for mixing to form said at least one of a polymer and therapeutic agent, said mixing portion being in controlled communication with said coating portion, said mixing portion comprising a mixing basket having an inner end portion operable to open to deliver said at least one of a polymer and therapeutic agent into the coating portion.

23. The apparatus of claim 22 wherein said apparatus comprises a drive means to rotate said chamber at a predetermined speed and by a predetermined angular amount.

24. The apparatus of claim 22 including drive means to effect mixing in said mixing portion.

25. The apparatus of claim 24 wherein said drive means comprises a magnetic drive unit.

26. The apparatus of claim 24 wherein said drive means comprises a drive socket for engagement with a mixer drive shaft in said mixing portion.

27. The apparatus of claim 22 including at least one of means to read, store, review and integrate information regarding one or more of the medical implant device, the polymer and the therapeutic agent; said apparatus further including means to control at least one of the mechanics, quality and documentation of the coating process.

28. The apparatus of claim 22 wherein said chamber is removable from said apparatus.

29. The apparatus of claim 22 wherein said medical implant device to be coated includes at least one of a binding, linking, absorbing and adsorbing pre-coating thereon.

30. The apparatus of claim 29 wherein the pre-coating comprises a functional peptide linker or hydroxyapatite.

31. The apparatus of claim 22 wherein said chamber includes a plurality of introduction ports.

32. The apparatus of claim 22 including one or more introduction ports positioned to communicate with one or more introduction ports in said at least one of said coating portion and said mixing portion.

33. The apparatus of claim 22 wherein said chamber is generally cylindrical in shape, the cylindrical chamber being positionable generally horizontal in said apparatus and being rotatable about an axis extending in the horizontal direction to effect a bathing or splashing of the said at least one of a polymer and therapeutic agent on the medical implant device in the coating chamber.

34. The apparatus of claim 22 wherein said chamber comprises a generally horizontal axis of rotation when positioned in said apparatus and wherein said mixing portion and said coating portion are attached to and in communication with said chamber and are oriented perpendicular to said horizontal axis.

35. The apparatus of claim 34 wherein said mixing portion and said coating portion are diametrically opposed to one another.

36. The apparatus of claim 34 wherein said mixing portion is positioned at a lower orientation than said coating portion for mixing the components of said at least one of a polymer and therapeutic agent, and wherein said apparatus is operable to rotate said chamber by a predetermined amount whereby said coating portion is positioned at a lower orientation than said mixing portion thereby effecting a flow of said at least one of a polymer and therapeutic agent into said coating portion to immerse and coat a medical implant device supported in said coating portion.

37. The apparatus of claim 22 wherein one or both of said coating portion and said mixing portion includes a heating means.

38. The apparatus of claim 33 wherein said coating portion includes a plurality of coating vanes.

39. The apparatus of claim 22 further comprising a source of light and/or microwave energy for penetrating said chamber to cure a coating on a medical implant device.

40. The apparatus of claim 31 wherein said apparatus controls the atmosphere of the coating chamber and comprises a source of at least one a predetermined type of gas, a gas under a desired pressure, or a vacuum which can be introduced into said chamber via the introduction ports.

41. The apparatus of claim 22 wherein said coating portion further includes a hotwire coating trimmer.

* * * * *